US010669535B2

(12) United States Patent
Pendergrast et al.

(10) Patent No.: US 10,669,535 B2
(45) Date of Patent: Jun. 2, 2020

(54) METHODS FOR THE ISOLATION OF EXTRACELLULAR VESICLES AND OTHER BIOPARTICLES FROM URINE AND OTHER BIOFLUIDS

(71) Applicant: Ymir Genomics LLC, Cambridge, MA (US)

(72) Inventors: Patrick Shannon Pendergrast, Cambridge, MA (US); Robert Scott Pendergrast, Chatham, NJ (US); John Stephen Pendergrast, Stockholm, NJ (US); Anna Irmina Markowska, Brookline, MA (US)

(73) Assignee: YMIR GENOMICS, LLC, Cambridge, MA (US)

( * ) Notice: Subject to any disclaimer, the term of this patent is extended or adjusted under 35 U.S.C. 154(b) by 266 days.

(21) Appl. No.: 15/501,068

(22) PCT Filed: Aug. 5, 2015

(86) PCT No.: PCT/US2015/043768
§ 371 (c)(1),
(2) Date: Feb. 1, 2017

(87) PCT Pub. No.: WO2016/022654
PCT Pub. Date: Feb. 11, 2016

(65) Prior Publication Data
US 2017/0252670 A1 Sep. 7, 2017

Related U.S. Application Data

(60) Provisional application No. 62/033,643, filed on Aug. 5, 2014, provisional application No. 62/033,644, filed on Aug. 5, 2014.

(51) Int. Cl.
C12N 15/10 (2006.01)
C07K 1/30 (2006.01)
C07K 14/705 (2006.01)
B01D 21/26 (2006.01)
B01D 9/00 (2006.01)
G01N 1/40 (2006.01)

(52) U.S. Cl.
CPC ....... C12N 15/1003 (2013.01); B01D 9/0054 (2013.01); B01D 21/26 (2013.01); C07K 1/30 (2013.01); C07K 1/303 (2013.01); C07K 1/306 (2013.01); C07K 14/705 (2013.01); G01N 1/4055 (2013.01); B01D 21/262 (2013.01); B01D 2009/0086 (2013.01)

(58) Field of Classification Search
CPC ................................................ C12N 15/1003
USPC ......................................................... 435/6.1
See application file for complete search history.

(56) References Cited

U.S. PATENT DOCUMENTS

| 5,155,018 A * | 10/1992 | Gillespie ............... B01D 15/08 |
| | | 435/6.16 |
| 5,328,603 A * | 7/1994 | Velander ............... B01J 20/291 |
| | | 210/198.2 |
| 2009/0258379 A1 | 10/2009 | Klein et al. |
| 2013/0337440 A1 | 12/2013 | Antes et al. |

FOREIGN PATENT DOCUMENTS

EP 2604704 6/2013

OTHER PUBLICATIONS

Pisitkun et al., "Identification and proteomic profiling of exosomes in human urine," PNAS, vol. 101, No. 36, Sep. 7, 2004, pp. 13368-13373.
Hoorn et al., "Prospects for urinary proteomics: Exosomes as a source of urinary biomarkers," Nephrology 2005; 10, 283-290.
Zhou et al., "Collection, storage, preservation, and normalization of human urinary exosomes for biomarker discovery," Kidney International (2006) 69, 1471-1476.
Gonzales et al., "Large-Scale Proteomics and Phosphorproteomics of Urinary Exosomes," J Am Soc Nephrol 20: 363-379, 2009.
European Patent Office, Extended European Search Report, European Patent Application No. 15830435.2, dated Mar. 15, 2018, 12 pages.
International Search Report issued in corresponding international Application No. PCT/US2015/043768, dated Nov. 23, 2015, 5 pages.
Written Opinion of the International Searching Authority issued in corresponding international Application No. PCT/US2015/043768, dated Nov. 23, 2015, 10 pages.

(Continued)

Primary Examiner — Jezia Riley
(74) Attorney, Agent, or Firm — Burns & Levinson LLP; Christopher R. Cowles

(57) ABSTRACT

Compositions and methods for the isolation of protein-nucleic acid complexes and microvesicles (collectively referred to as "bioparticles") released by mammalian cells into body fluids or cell culture media are provided. Isolated bioparticles of the invention contain biological molecules that are useful as diagnostic/prognostic biomarkers or for identification of therapeutic targets (e.g., disease or disorder-associated miRNAs). The isolation of biological molecules as described herein results in purification and concentration of the molecules. Methods for producing bio fluids that are free of detectable bioparticles, that are largely depleted of bioparticles, or that possess a reduced concentration of bioparticles compared to a bio fluid starting material (collectively termed "bioparticle-depleted") are also provided. Isolation of bioparticle-depleted biofluid is useful, e.g., in experimental systems where it is desirable to use a biofluid that does not contain endogenous bioparticles, or has been substantially depleted of endogenous bioparticles, from the source material.

23 Claims, 27 Drawing Sheets

(56) References Cited

OTHER PUBLICATIONS

International Preliminary Report on Patentability, International Application No. PCT/US2015/043768, dated Aug. 5, 2015.

* cited by examiner

Figure 2

| Method | Available Kits? | Isolates | Pros | Cons |
|---|---|---|---|---|
| Ultracentrifuge | No | Microvesicles, Protein/NA complexes | Gold Std, High yield, purity, complex yield | Laborious, requires UC |
| Filtration | Exosome Diagnostics Millpore | Microvesicles Protein/NA complexes?? | Fast and Easy | scalability, complexity expense |
| Precipitation | SBI, Exiqon | Microvesicles, Protein/NA complexes | Easy | poor yield, poor purity |
| Binding Column | Norgen | Microvesicles Protein/NA complexes? | Fast and Easy | can't purify whole exosomes, complexity? |

Figure 3

| Company | Whole Exosome | Exosome Protein | Exosome RNA | Time | Price /Sml | Urine Specific | Comment |
|---|---|---|---|---|---|---|---|
| LifeTech | No | Yes | Yes | >1hr | $3.98 | Included | Phenol |
| Norgen Bio | No | Yes-2 kits | Yes | >1hr | $0.80 | Specific | Low Purity? |
| System Bio | No | Yes | Yes | >12hr | $5.76 | Included | Low Yield |
| NEP* | Yes | Yes | Yes | <1hr | $49.9 | Included | |
| Qiagen/ED* | Maybe | No | Yes | 25min | $9.97 | No | Scalable? |
| Exiqon* | No? | No? | Yes | >1.5hr | $2.46 | Included | Low Yield? |
| Amicon-Microvesicle Enrichment* | Yes | Yes | Yes | >1hr | $0.76 | No | Only media Low Purity |

Concentrated Urine Sample
(natural high protein content)

Dilute Urine Sample
(natural low protein content)

The same sample diluted 2x (lane 2), 4x (lane 3), and 8x (lane 4)

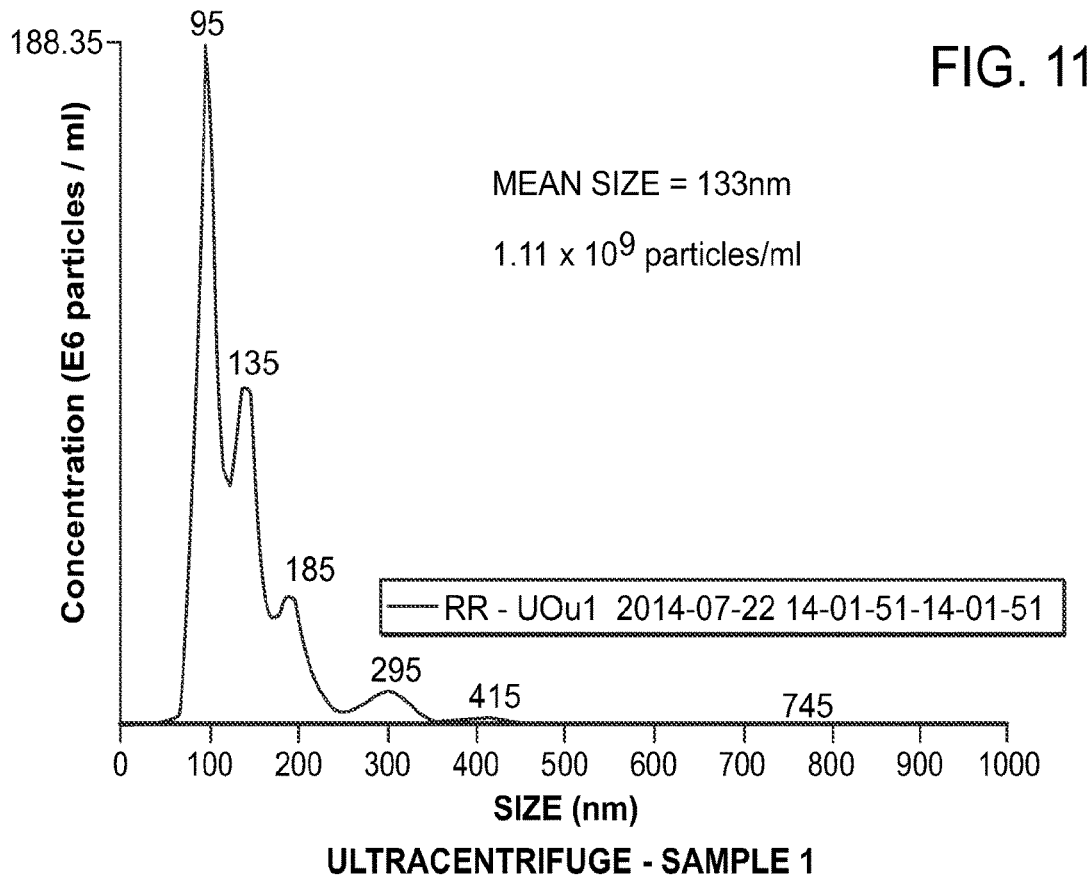
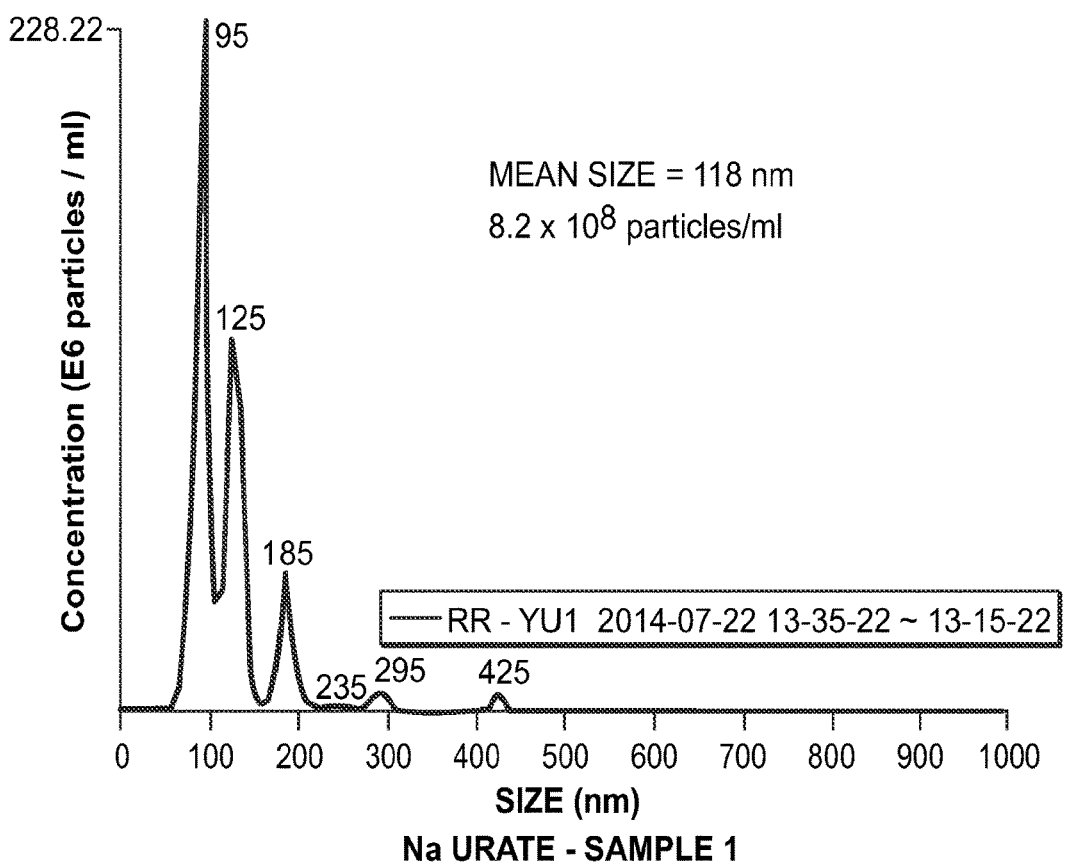
FIG. 11

A.

B.

A.

EXPERIMENTAL DESIGN

B.

DATA

DE Purification of extra-cellular vesicles from 3 mls of Urine and 5 mls of Saliva

Figure 23

| Grade | M | W DE | FP4 DE | FW60 DE | W DE | Cel-S DE | FN6 DE | FP22 DE | AW2 DE |
|---|---|---|---|---|---|---|---|---|---|
| AQP-2G | | | | | | | | | |
| CD9 | | | | | | | | | |
| Permeability (D) | | ? | .3 | 5 | ? | .05 | .02 | .05 | .14 |
| Pore Size (uM) | | 1.2 | ? | ? | 1.2 | 1.5 | ? | ? | ? |
| Particle Dia (uM) | | 10 | 15 | 48 | 10 | ? | 12 | 8.5 | 11 |
| SiO2% | | 89% | 92% | 89% | 89% | 86% | 89% | 93% | 93% |
| Treatment | | N | C | C | N | N | N | C | Acid Washed |

Figure 24

| Grade | M | W DE | Cel-S DE | FN6 DE | FP22 DE | AW2 DE | |
|---|---|---|---|---|---|---|---|
| Rab5 | | | | | | | |
| CD9 | | | | | | | |
| Perm. (D) | | ? | .05 | .02 | .05 | .14 | |
| Pore Size (uM) | | 1.2 | 1.5 | ? | ? | ? | |
| Part. Dia (uM) | | 10 | ? | 12 | 8.5 | 11 | |
| SiO2% | | 89% | 86% | 89% | 93% | 93% | |
| Treatment | | N | N | N | C | Acid Washed | |

N = Natural
C = Calcinated

Figure 25

| Grade | Sigma Silica | M | W DE | M | Perlite: 17-S | 23-S | 27-M |
|---|---|---|---|---|---|---|---|
| AQP-2G | | | ■■■ | | ▬ | ▬▬ | ▬▬ |
| Rab5 | | | ▬▬ | | | ▬▬ | ▬▬ |
| Perm. (D) | ? | | ? | | 3 | 1 | .2 |
| Pore Size (uM) | .006 | | 1.2 | | ? | 8-10 | 3-5 |
| Part. Dia (uM) | ~50 | | 10 | | ? | ? | ? |
| SiO2% | ? | | 89% | | 73% | 73% | 73% |
| Treatment | NA | | N | | Heat | Heat | Heat |

METHODS FOR THE ISOLATION OF EXTRACELLULAR VESICLES AND OTHER BIOPARTICLES FROM URINE AND OTHER BIOFLUIDS

CROSS-REFERENCE TO RELATED APPLICATIONS

This application is the U.S. national stage pursuant to 35 U.S.C. § 371, of United States International Application Ser. No. PCT/US2015/043768, filed Aug. 5, 2015 and published in English on Feb. 11, 2016 as publication WO2016/022654 A1, which is related to U.S. Provisional Patent Application Ser. No. 62/033,643, entitled "Methods for the Isolation of Cell-Free Protein-Nucleic Acid Complexes and Microvesicle Bioparticles from Liquids", which was filed Aug. 5, 2014, and to U.S. Provisional Patent Application Ser. No. 62/033,644, entitled "Methods for the Isolation of Cell-Free Protein-Nucleic Acid Complexes, Biomarkers and Microvesicle Bioparticles from Urine", which was filed Aug. 5, 2014. The entire contents of these patent applications are hereby incorporated by reference herein.

FIELD OF THE INVENTION

The invention relates to the field of cell biology, and in particular, to the study of circulating, cell-free, membrane-bound structures and protein-nucleic acid complexes that are produced and released by cells. The term "bioparticles" collectively describes these and other cell-free entities including proteins, non-vesicular lipids, DNA, RNA, and certain small molecules. The invention also relates to compositions and methods for the isolation of bioparticles produced by cells, which are useful, for example, in diagnostic, prognostic, and therapeutic applications.

BACKGROUND OF THE INVENTION

A diverse collection of protein-nucleic acid complexes and membrane-bound structures are released from mammalian cells during the course of their life and death (FIG. 1). Such compositions are broadly termed "bioparticles". Exemplary protein-nucleic acid complexes include Ago2-microRNA complexes, which are known to exist as stable complexes in cell-free biofluids (Arroyo et al. Argonaute2 Complexes Carry a Population of Circulating MicroRNAs Independent of Vesicles in Human Plasma (2011) PNAS 108:5003-5008). Such complexes are released into the fluids of a subject (e.g., urine, blood, etc.) according to the status of the cell and/or upon degradation of the cell after death.

Membrane-bound structures (also known as extracellular vesicles or microvesicles) released from or otherwise derived from cells include exosomes, microvesicles, apoptotic bodies, and high density lipoprotein (HDL)-particles. (It is noted that the terms "extracellular vesicles" and "microvesicles" are used interchangeably herein to describe all cell-derived membrane-bound structures.)

The function of extracellular vesicles is not clearly understood, although they are theorized to act as nano-shuttles for the transport and delivery of information from one location and/or cell type to distant locations and/or other cell types (Mathivanan and Simpson, "Exosomes: extracellular organelles important in intercellular communication," J. Proteomics 73(10):1907-1920 (2010)). Also, they are theorized to be involved in a wide variety of physiological processes, including cardiac disease, adaptive immune responses to pathogens, and in tumor biology. It is suggested that microvesicles may play roles in tumor immune suppression, metastasis, and tumor-stroma interactions. Microvesicles are thought to play a role in immune system cellular communication, for example, involving dendritic cells and B cells (Raposo et al., J. Exp. Med. 183 (1996) 1161).

The ubiquitous presence of circulating microvesicles in body fluids, their association with a broad range of physiological processes, as well as their elevated levels in human disease, suggest that microvesicles can potentially serve as tools in molecular medicine as measures of physiological state, disease diagnostics, and possibly therapeutic targeting.

Although the study of microvesicles/exosomes had been greatly advanced with the development of analytical systems such as nanoparticle tracking analysis (NTA) and fluorescent nanoparticle tracking analysis (FNTA; see (i) Van der Pol et al., "Optical and non-optical methods for detection and characterization of microparticles and exosomes," Journal of Thrombosis and Haemostasis (2010), doi: 10.1111/j.1538-7836.2010.04074.x; (ii) Dragovic et al., "Sizing and phenotyping of cellular vesicles using Nanoparticle Tracking Analysis," Nanomedicine: Nanotechnology, Biology and Medicine (2011), doi:10.1016/j.nano.2011.04.003, other technical challenges remain.

One of the significant technical challenges in current research in microvesicles is the problem of how to efficiently isolate the microvesicles from various sources. Current methodologies to isolate secreted microvesicles, including but not limited to exosomes, are constrained by technical limitations and other drawbacks. These known methodologies are labor intensive, time-consuming, costly, and can be unreliable for different fluids; see Tauro et al., "Comparison of ultracentrifugation, density gradient separation, and immunoaffinity capture methods for isolating human colon cancer cell line LIM1863-derived exosomes," Methods 56(2):293-304 (print February 2012, Epub Jan. 21, 2012), doi:10.1016/j.ymeth.2012.01.002.

Historically, ultracentrifugation is the traditional method for microvesicle isolation. Generally, centrifugation is the process whereby a centrifugal force is applied to a mixture, whereby more-dense components of the mixture migrate away from the axis of the centrifuge relative to other less-dense components in the mixture. The force that is applied to the mixture is a function of the speed of the centrifuge rotor, and the radius of the spin. In most applications, the force of the spin will result in a precipitate (a pellet) to gather at the bottom of the centrifuge tube, where the remaining solution is properly called a "supernate" or "supernatant." In other similar applications, a density-based separation or "gradient centrifugation" technique is used to isolate a particular species from a mixture that contains components that are both more dense and less dense than the desired component (e.g., OptiPrep™).

During the circular motion of a centrifuge rotor, the force that is applied is the product of the radius and the angular velocity of the spin, where the force is traditionally expressed as acceleration relative to "g," the standard acceleration due to gravity at the Earth's surface. The centrifugal force that is applied is termed the "relative centrifugal force" (RCF), and is expressed in multiples of "g" (or "×g").

The centrifugation procedures that have been used to isolate circulating microvesicles can incorporate as many as five centrifugation steps, with at least two of these spins requiring centrifugal forces in excess of 100,000×g for several hours. Generally, ultracentrifugation is centrifugation conditions that produce forces in excess of 100,000×g. These ultracentrifugation procedures are time consuming and labor intensive, and furthermore, are constrained by the requirement for expensive ultracentrifugation equipment. They can also be unreliable for certain fluids (see FIGS. 2 and 3).

Size exclusion chromatography can also be used to isolate microvesicles, for example, by using a Sephadex™ G200 column matrix. This approach is also time consuming and the yields are inconsistent. It also may be difficult or expensive to scale up to larger quantities of biofluid. Finally, these columns can be clogged by viscous biofluids.

Selective immunoaffinity capture (including immuno-precipitation) can also be used to isolate circulating microvesicles, for example, by using antibodies directed against the epithelial cell adhesion molecule, a type-1 transmembrane cell-surface protein (also known as EpCAM, CD326, KSA, TROP1). The anti-EpCAM antibodies can be coupled to magnetic microbeads, such as Dynabeads® magnetic beads. This method has very low yields compared to other methods, and is costly due to the use of the immuno-reagents and magnetic beads, and further, these system reagents cannot be reused for subsequent isolations.

What is needed in the art are methods for the rapid and inexpensive isolation of extracellular membrane particles, including microvesicles, exosomes, and apoptotic bodies, as well as any accompanying biomarkers, especially from biofluids such as urine. It would also be useful to have such a method that would isolate membrane-free protein-nucleic acid particles, cell-free messenger RNA, and cell-free DNA as well. Finally, for many applications, it would be desirable to obtain intact bioparticles for use in mechanistic, vaccine-related, delivery-related and therapeutic studies.

Such methods will ideally use common laboratory reagents and apparatus, and will not require high-speed centrifugation, such as ultracentrifugation. In addition, methods that provide higher yields than current methods are also needed, allowing for the isolation of important biomarkers and/or therapeutic targets from a smaller volume of sample.

Furthermore, what is also needed in the art are methods for generating cell culture media that are free of endogenous bioparticles, or have reduced concentrations of endogenous bioparticles compared to traditional complete media.

SUMMARY OF THE INVENTION

The current invention is based, at least in part, upon discovery of a means for isolating bioparticles from liquid sample (e.g., biofluid) using several approaches, including a crystal-promoting and/or precipitation method and an apparent matrix-binding method that is optionally suitable for columns (without wishing to be bound by theory, the matrix-binding method appears to exploit pore sizes of certain materials to effect enrichment, such as the pore sizes found in porous beads, e.g., siliceous beads such as diatomaceous earth and perlite). In certain aspects, the invention provides methods for the rapid and inexpensive isolation of bioparticles: specifically, membrane-bound vesicles, cell-free protein-nucleic acid complexes, cell-free mRNA, and/or cell-free DNA can be isolated from almost any fluid. These methods use common laboratory equipment and reagents. They do not require high-speed centrifugation, such as ultracentrifugation. They do not require expensive membranes, antibodies, antibody fragments, beads, or sophisticated columns. Such methods produce a higher yield of bioparticles and known bioparticle markers than many other methods. The methods do not co-purify prohibitive amounts of PCR inhibitors that would complicate downstream nucleic acid analysis. In some embodiments, the methods allow for isolation of intact microvesicles, enabling mechanistic, delivery, vaccine-related, immunostimulation-related and therapeutic downstream studies.

The instant methods were primarily developed for bioparticle isolation from urine but can be used upon any biofluid, such as, but not limited to, blood plasma, blood serum, cerebrospinal fluid (CSF), saliva, synovial fluid, amniotic fluid, and cell culture media. The methods of the invention are even capable of isolating microvesicles from water (see below Example). The microvesicles isolated by the methods of the invention possess characteristics of true microvesicles, as assayed by protein markers, small RNAs, and Nanoparticle tracking Analysis (NTA). Also, analysis of the microRNAs isolated by the methods of the invention suggests that protein-nucleic acid complexes are also isolated.

In certain embodiments, the invention provides methods for isolating released bioparticles from whole urine samples, where those methods comprise i) treating whole urine samples with the reducing agent TCEP (tris(2-carboxyethyl) phosphine, optional; TCEP protects against the loss of microvesicles in the subsequent low speed spin), ii) spinning the urine samples in a low speed spin (typically 1000×g for typically 5 minutes) to remove cellular contamination and debris (contained in the pellet), iii) applying the crystal and/or precipitation inducing reagent Monosodium Urate to the supernatant of the previous spin, iv) incubating the mixture, typically on ice or 4 degrees and typically for 15 minutes, v) centrifuging the mixture to form a pellet and a supernatant, most advantageously, in a low speed centrifugation, vi) removing the supernatant after the spin and, vii) recovering the pellet by resuspending in a resuspension solution.

In certain other embodiments, the secreted bioparticles that are isolated are exosomes. In some embodiments, isolation of exosomes is confirmed by determining whether or not the isolated material is enriched for protein or nucleic acid makers that are known to preferentially segregate with exosomes. Confirmation can also be obtained by physical analysis such as NTA or electron microscopy where exosomes having an average diameter between about 40 nm and about 150 nm is consistent with exosome isolation.

In certain embodiments, the secreted bioparticles are protein-nucleic acid complexes such as AGO2-miRNA particles. Evidence for these particles can be obtained by assaying for specific miRNAs known to take part in such complexes or by assaying for AGO2 protein.

In certain embodiments, the secreted bioparticles are cell-free mRNA particles. Evidence for these particles can be obtained (and indeed was obtained) via assay for specific mRNAs.

In some embodiments of the invention, another reducing agent other than TCEP can be used, such as DTT.

In some aspects of the invention, Uric Acid or other salts of Uric Acid (e.g. Lithium, Calcium, or Potassium Urate—see FIG. 19) can be used instead of Monosodium Urate as the crystal/precipitation-inducing agent.

The crystallization/precipitation-inducing agent can be prepared and administered either as a solid, slurry, or a liquid (Monosodium Urate, uric acid and other uric acid salts can be solubilized into basic buffers such as NaOH).

In certain embodiments, the invention provides methods for isolating released bioparticles from whole urine samples, where those methods comprise i) spinning the urine samples in a low speed spin (typically 1000×g for typically 5 minutes) to remove cellular contamination and debris (contained in the pellet), ii) applying porous beads (e.g., siliceous beads such as diatomaceous earth (DE) and/or perlite) to the cell-free urine sample, or alternatively applying the cell-free urine to column containing porous beads (optionally, siliceous beads, such as diatomaceous earth and perlite) iii) incubating the mixture, typically at room temperature and typically for 15 minutes, iv) centrifuging the mixture to form a pellet and a supernatant, most advantageously, in a tow speed centrifugation, vi) removing the supernatant after the spin and, vii) recovering the pellet by resuspending the porous beads in a resuspension solution.

The invention is superior to ultracentrifugation methods because i) it does not require an expensive ultracentrifuge, ii) it is significantly faster, iii) it does not lose as many microvesicles in the first centrifugation step, and iv) as judged by some markers for urine microvesicles and extra-cellular miRNA, has a higher yield, especially in more dilute urine samples (see FIGS. 4 and 5).

The invention is also superior to existing commercial and academic precipitation methods in that i) it does not lose as many microvesicles in the first centrifugation step (see FIG. 20), ii) the incubation time is significantly shorter, iii) the crystal/precipitation-inducing agent or the porous beads are significantly less expensive than other precipitation-inducing reagents, and iv) as judged by some markers for urine microvesicles, has a higher yield, especially in more dilute samples (see FIGS. 4 and 5).

Certain embodiments of the invention are superior to existing precipitation, column and filtration methods, in that i) they do not lose as many microvesicles in the first centrifugation step, ii) do not require expensive column housing, column packing, or filters, iii) can be significantly faster than, iv) can be easily scaled up to large volumes of biofluid and v) as judged by some markers for urine microvesicles and extra-cellular miRNA, have a higher yield.

Certain embodiments of the invention are superior to all other tested methods known in the art, in that the instant methods isolate from urine >50-fold more of the well-known urine microvesicle biomarker Aquaporin-2. Aquaporin-2 has been used as a general biomarker for urine microvesicles and also as a specific biomarker for various diseases and drugs such as, but not limited to, Nephrogenic Diabetes Insipidus, Hepatic Cirrhosis, Congestive Heart Failure, Lithium Nephrotoxicity, Vasopressin activity, and V2R Antagonist activity (see Sasaki Aquaporin 2: From its Discovery to Molecular Structure and Medical Implications (2012) Molecular Aspects of Medicine 33:535).

As certain embodiments of the invention are capable of isolating microvesicles suspended even in saliva or unbuffered water alone, in some embodiments the liquid sample can be any biofluid including cell culture media; i.e., a culture media that has been used to culture cells. Other biofluids include, but are not limited to whole blood, blood serum, blood plasma, urine, saliva, sputum, breast milk, ascites fluid, synovial fluid, amniotic fluid, semen, cerebrospinal fluid, follicular fluid and tears.

In other aspects, the invention also provides methods for producing biofluids or serum that are depleted or partially depleted of endogenous microvesicles, or the microvesicles are below the limits of detection. These methods comprise i) spinning the biofluid samples in a low speed spin (typically 1000×g for typically 5 minutes) to remove cellular contamination and debris (contained in the pellet), ii) applying the crystal/precipitation inducing reagent Monosodium Urate or porous beads (e.g., siliceous beads such as DE and/or perlite) to the supernatant of the previous spin, iii) incubating the mixture, iv) centrifuging the mixture to form a pellet and a supernatant, most advantageously, in a low speed centrifugation, recovering the supernatant after the spin, and (v) transferring the supernatant to a suitable container, where the supernatant is the microvesicle-depleted biofluid.

In one aspect, the invention provides a method for isolating bioparticles from a liquid sample, the method involving: a) obtaining a liquid sample from a subject or cell culture; b) contacting the liquid sample with a crystal/precipitation-inducing agent under conditions suitable to allow for crystal formation and/or precipitation, thereby creating an admixture; c) incubating the admixture for a period of time sufficient to allow for crystal formation and/or precipitation; and d) separating the admixture to obtain a particle fraction containing bioparticles, thereby isolating bioparticles from the liquid sample.

In one embodiment, the crystal/precipitation-inducing agent is monosodium urate, uric acid, a salt thereof and/or a combination thereof.

In another embodiment, the admixture is present in an array of admixtures. Optionally, the array is a 96 well array.

In one embodiment, the admixture volume is less than about 1 ml. In another embodiment, the step (d) of separating includes centrifugation. Optionally, the centrifugation creates a pellet that is subsequently resuspended in a solution.

In one embodiment, the period of time of step (c) is at least 1 minute, at least 5 minutes, at least 10 minutes, 1-5 minutes, 5-10 minutes, 10-15 minutes, 15-30 minutes, 30 minutes or less, 15 minutes or less, 10 minutes or less, or 5 minutes or less.

In another embodiment, the isolated bioparticles include microvesicles. Optionally, the microvesicles include exosomes.

In one embodiment, the liquid sample includes a biofluid. In an additional embodiment, the liquid sample includes a fluid that is whole blood, blood serum, blood plasma, urine, saliva, sputum, breast milk, ascites fluid, synovial fluid, amniotic fluid, semen, cerebrospinal fluid, follicular fluid and/or tears.

In another embodiment, the isolated microvesicles include a population of microvesicles possessing an average diameter of between about 40 nm and about 150 nm.

In one embodiment, the pellet is resuspended in a volume of solution that is less than the starting volume of the liquid sample.

In another embodiment, the resuspended pellet solution is enriched for at least one marker known to correlate with exosomes. Optionally, the at least one marker is a protein marker or a nucleic acid marker.

In one embodiment, the crystal/precipitation-inducing agent is monosodium urate.

In another embodiment, the crystal/precipitation-inducing agent is uric acid.

In an additional embodiment, the crystal/precipitation-inducing agent is a salt of uric acid.

In certain embodiments, the centrifugation is a low-speed centrifugation. Optionally, the centrifugation is at about 2,000×g.

Another aspect of the invention provides a method for isolating bioparticles from a urine sample, the method involving: a) obtaining a urine sample from a subject; b) contacting the urine sample with a whole urine prespin treatment solution, thereby creating a first admixture; c) separating the first admixture to create a pellet and a supernatant; d) removing the pellet; e) contacting the supernatant with a crystal/precipitation-inducing agent under conditions suitable to allow for crystal formation and/or precipitation, thereby creating a second admixture; f)

incubating the second admixture for a period of time sufficient to allow for crystal formation and/or precipitation; g) separating the second admixture to obtain a particle fraction containing bioparticles, thereby isolating bioparticles from the urine sample.

In one embodiment, the second admixture volume is less than about 1 ml.

In certain embodiments, the whole urine prespin treatment solution includes a reducing agent and/or a buffer that lowers the pH of the sample below 6.

In one embodiment, the whole urine prespin treatment solution includes TCEP.

In another embodiment, either or both of the separating steps (c) and (g) involve centrifugation.

In one embodiment, the pellet of step (g) is resuspended in a volume of solution that is less than the starting volume of the liquid sample. In a related embodiment, the resuspended pellet solution of step (g) is enriched for at least one marker known to correlate with exosomes.

In certain embodiments, either or both of the separating steps (c) and (g) include a low-speed centrifugation. Optionally, either or both of the separating steps (c) and (g) involve centrifugation at about 2,000×g.

An additional aspect of the invention provides a method for reducing the microvesicle content of a liquid sample from a subject or cell culture, the method involving: a) obtaining a liquid sample from a subject or cell culture; b) contacting the liquid sample with a crystal/precipitation-inducing agent under conditions suitable to allow for crystal formation and/or precipitation, thereby creating an admixture; c) incubating the admixture for a period of time sufficient to allow for crystal formation and/or precipitation; d) separating the admixture to obtain a particle fraction and a liquid fraction and isolating the liquid fraction, thereby reducing the microvesicle content of a liquid sample from a subject or cell culture.

In one embodiment, the admixture volume is less than about 1 ml.

In certain embodiments, the liquid sample includes in vitro cell culture serum.

In another embodiment, the liquid sample includes serum. Optionally, the serum is selected from the group consisting of a bovine serum, a horse serum, a human serum, a rat serum, a mouse serum, a rabbit serum, a sheep serum, a goat serum, a lamb serum, a chicken serum and a porcine serum. In a related embodiment, the serum is a fetal bovine serum.

In some embodiments, the separating includes a low-speed centrifugation. In one embodiment, the separating includes centrifugation at about 2,000×g.

Another aspect of the invention provides a method for isolating Aquaporin-2 (AQ-2) from a urine sample, the method involving: a) obtaining a urine sample from a subject; b) contacting the urine sample with a crystal/precipitation-inducing agent under conditions suitable to allow for crystal formation and/or precipitation, thereby creating an admixture; c) incubating the admixture for a period of time sufficient to allow for crystal formation and/or precipitation; d) separating the admixture to obtain a particle fraction containing AQ-2, thereby isolating AQ-2 from the urine sample.

A further aspect of the invention provides a method for isolating secreted AQ-2 from a urine sample the method involving: a) obtaining a urine sample from a subject; b) contacting the urine sample with a whole urine prespin treatment solution, thereby creating a first admixture; c) separating the first admixture to create a pellet and a supernatant; d) removing the pellet; e) contacting the supernatant with a crystal/precipitation-inducing agent under conditions suitable to allow for crystal formation and/or precipitation, thereby creating a second admixture; f) incubating the second admixture for a period of time sufficient to allow for crystal formation and/or precipitation; g) separating the second admixture to obtain a particle fraction containing AQ-2, thereby isolating AQ-2 from the urine sample.

In certain embodiments, the second admixture is present in an array of second admixtures. Optionally, the array is a 96 well array.

In one embodiment, the second admixture volume is less than about 1 ml.

In another aspect, the invention also provides a kit for isolating bioparticles from a liquid sample that includes a crystal/precipitation-inducing agent, and instructions for its use. In one embodiment, the liquid sample is a urine sample.

A further aspect of the invention provides a method for isolating bioparticles from a urine sample, the method involving: a) obtaining a urine sample from a subject; b) contacting the urine sample with a whole urine prespin treatment solution, thereby creating a first admixture; c) separating the first admixture to create a pellet and a supernatant; d) removing the pellet; e) contacting the supernatant with porous beads, thereby creating a second admixture; incubating the second admixture for a period of time sufficient to allow for porous bead-bioparticle complex formation; g) separating the second admixture to obtain a particle fraction containing bioparticles, thereby isolating bioparticles from the urine sample.

In certain embodiments, the whole urine prespin treatment solution includes a reducing agent and/or a buffer that lowers the pH of the sample below 6. Optionally, the whole urine prespin treatment solution includes TCEP.

In one embodiment, either or both of the separating steps (c) and (g) comprise centrifugation.

In another embodiment, the separation step (g) includes an ultracentrifuge spin at speeds >75,000×g.

In certain embodiments, the whole urine prespin treatment solution includes $CaCl_2$, $CaCO_3$ and/or Hydroxyapatite at a concentration >10 mM.

In another embodiment, the porous beads are porous siliceous beads, optionally diatomaceous earth or perlite.

In certain embodiments, the pore size of the porous beads is about 0.1 to 10 microns, optionally about 0.2 to 5 microns, optionally about 0.5 to 2 microns, optionally about 1 micron.

In related embodiments, the separating steps (c) and (g) involve low speed centrifugation spins below 18,000×g.

In one embodiment, the whole urine prespin treatment solution includes TCEP immobilized on beads.

In another embodiment, the second admixture contains the supernatant resulting from separating step (c) with the TCEP immobilized beads removed.

In an additional aspect, the invention also provides a kit for isolating bioparticles from a urine sample that includes a whole urine prespin treatment solution and porous beads, and instructions for its use.

A further aspect of the invention provides a method for isolating bioparticles from a liquid sample, the method involving: a) obtaining a liquid sample from a subject or cell culture; b) contacting the liquid sample with a crystal/precipitation-inducing agent under conditions suitable to allow for crystal formation and/or precipitation, and porous beads, thereby creating an admixture; c) incubating the admixture for a period of time sufficient to allow for crystal formation and/or precipitation; and d) separating the admixture to obtain a particle fraction containing bioparticles, thereby isolating bioparticles from the liquid sample.

An additional aspect of the invention provides a method for isolating bioparticles from a liquid sample, the method involving: a) obtaining a liquid sample from a subject or cell culture; b) contacting the liquid sample to a column containing porous beads and/or a crystal/precipitation-inducing agent under conditions suitable to allow for crystal formation and/or precipitation; and c) eluting fractions from the column to obtain one or more bioparticle-enriched fractions, thereby isolating bioparticles from the liquid sample. (It is contemplated that either or both of (1) porous beads and (2) crystal/precipitation-inducing agents as described herein, alone or in combination, can also be employed effectively/ with advantage in column formats. E.g., where a crystal/ precipitation-inducing agent is applied to a column, the components (e.g., beads or other solid component particles of art-recognized columns) of such a column need not be porous; similarly, columns that include porous beads such as those described herein are contemplated as effective for bioparticle isolation, even in the absence of crystal/precipitation-inducing agents.)

BRIEF DESCRIPTION OF THE DRAWINGS

FIG. 2 shows a comparison of exemplary methods used and/or proposed for isolation of microvesicles. Notably, most such methods are optimized for isolation from blood serum or plasma of a subject.

FIG. 3 shows a comparison of commercial kits available for microvesicle isolation. Asterisks indicate kits released in 2014. Boxed regions indicate potential drawbacks for each kit.

FIG. 7A shows a Bioanalyzer gel of small RNA isolated from a single 10 ml first void clean catch by ultracentrifugation (UC; half of the sample) and Ymir Genomics' Na Urate protocol (Y; half of the sample). FIG. 7B shows a Bioanalyzer gel trace of small RNA isolated from a single first void clean catch by ultracentrifugation (UC) in red and Ymir Genomics' Na Urate protocol (Ymir) in green. FIG. 7C shows relative amounts of 3 miRNAs known to be found in human urine. Methods: RNA was isolated from urinary vesicle preps (UC and Y) with mirVANA Kit (LifeTechnologies). Small RNA quality and concentration were determined using Agilent 2100 Bioanalyzer (Agilent Technologies, Santa Clara, Calif.) and Small RNA Kit (Agitent). RT-quantitative PCR. cDNA was synthesized from urinary vesicle RNA using the TaqMan Micro RNA RT Kit (LifeTechnologies) according to the manufacturer's instructions. qPCR was performed using TaqMan Gene Expression Master Mix (Life Technologies). Primers for hsa-mir-10b, hsa-mir-223, and hsa-mir-200c were obtained from Life Technologies.

FIG. 11 shows that Na Urate isolated whole exosomes: the NanoSight nanoparticle tracking device measured the number and size of vesicles in a solution. Methods: A 1 ml sample of first void clean catch urine was split in two. Half was subjected to Na Urate precipitation/crystallization (Method Y, right panel; see example 1) and half was subjected to standard ultracentrifugation. Both methods yielded particles of very similar size and shape, as judged by nanotracker particle sizing and counting. Vesicles were also isolated by ultracentrifugation as per FIG. 4. Nanoparticle Tracking Analysis. Vesicles, diluted in PBS, were analyzed by nanoparticle tracking using the NanoSight NS300 system (Malvern Instruments, Malvern, UK) equipped with 405 nm laser. Videos were collected and analysed using the NTA software (version 3.0 0060).

In FIG. 18A, an immunoblot using Mabs for vesicle markers Aquaporin 2, Rab5, and CD9. A single first void clean catch urine sample was divided into 6,200 ul portions and bioparticles were isolated using 96-well plate protocol (lanes 1-5 which are identical replicates towards precision data) and the standard test tube protocol (lane 6 (tube format)). RNA preps were made using the standard protocol (tube format) or 96-well plate protocol (96 Well Format) from multiple 200 ul aliquots from a single first void clean catch urine sample. The preps were subjected to qRT-PCR with Life Technologies miRNA probes for mir-200c. The 96-well plate format was identified as more efficient at isolating mir-200c than the standard tube format.

exposed to Diatomaceous Earth protocol, or 3) exposed to Silica particles as a control. The resulting preps were loaded onto a SDS PAGE gel transferred to Nitrocellulose and immunostained with antibodies specific for vesicle markers Aquaporin 2 and CD9. Protocol: 1 gram of Diatomaceous Earth or Control Silica particles were washed twice in PBS and then resuspended in 10 mls of PBS plus protease inhibitors. After vigorous vortexing, 150 ul of each slurry were pipetted into separate 3 ml aliquots of a cell-free urine sample in 15 ml polypropylene tubes. The tubes were rotated slowly for 30 minutes then spun at 1500 g for 2 minutes. The urine supernatant was discarded and the pellets were washed 2× with 3 mls of PBS. After the second wash the pellets were suspended in 100 ul of Laemmli buffer, boiled for 3 minutes and 50 ul of each was loaded onto a SDS PAGE gel. "Just Spin" control used the same protocol except no DE was added—showing that DE is required.

Figure 21:
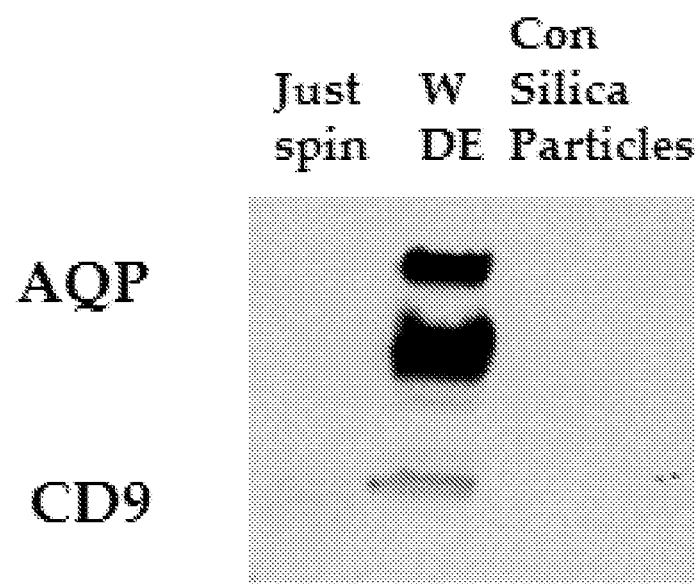
FIG. 21 shows that Diatomaceous Earth (DE) isolated vesicle protein markers from urine, whereas control silica did not. A single 9 ml first void clean catch urine sample was split in three and either 1) subjected to 2×1500 g spin, 2)
Figure 22:
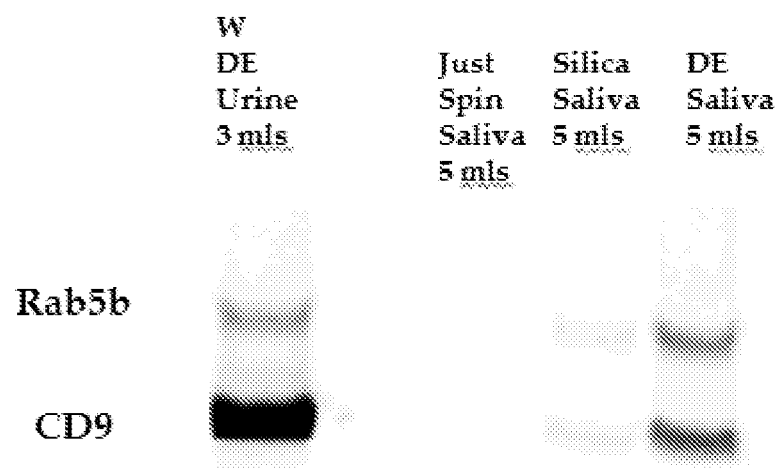

FIG. 22 shows that Diatomaceous Earth (DE) isolated saliva exosomes. immunoblot was performed with Mabs specific for vesicle markers Rab5 and CD9. Lane 1; bioparticle prep of 3 ml urine sample using DE (protocol as per FIG. 21), Lane 2; blank, Lane 3; 2×1500 g spin of 5 mls of cell free saliva, Lane 4; 5 mls cell-free urine treated with silica particles, Lane 5; 5 mls cell-free urine treated with Diatomaceous Earth. Saliva Protocol: 7.5 mls of saliva was diluted with 7.5 mls of PBS. Then it was spun 2×2000 g to remove cells, cell debris, and mucous. The resulting supernatant was split into 3, 5 ml aliquots. One aliquot (negative control) was spun two more times at 1500 g. Either 150 ul of silica beads or Diatomaceous Earth prepped as per FIG. 21 legend were added to the other two aliquots and then processed as per FIG. 21.

FIG. 23 shows that DE (optionally non-calcinated (N) and low permeable/small pore size) isolated EVs from urine. It was noted that the calcinated and larger pore diameter DE Grades worked the worst; C=calcinated; N=non-calcinated. Permeability was measured in Darcies (the higher the value, the more permeable). A single first void clean catch urine sample was split into 5 ml aliquots in 15 ml polypropylene tubes and exposed to 300 ul of a slurry (1 g into 10 mls of PBS) of different grades of Diatomaceous Earth acquired from several sources (see below). The mixture was incubated at RT for 20 minutes then the DE was removed from the mixture by a 3 minute 1500×g spin (supernatant poured off). The treated DE was washed 2× by 5 mls of PBS then suspended in 150 ul of Laemmli buffer. 50 ul of this was run on SDS PAGE gel and transferred to Nitrocellulose. The Nitrocellulose was probed with Mabs specific for extra-cellular vesicle markers CD9 and Aquaporin 2. Shown are signals from glycosylated. Aquaporin-2 and CD9 as judged by MW and important properties (if known) of each grade of DE. Grades and sources of Diatomaceous Earth: W=Natural Food Grade DE from PermaGuard; FP-4=Calcinated DE from Ep Minerals (Reno, Nev.); FW-60=Calcinated DE from Ep Minerals (Reno, Nev.); FP-22=Calcinated DE from Ep Minerals (Reno, Nev.); FN-6=Natural DE from Ep Minerals (Reno, Nev.); Cel-S=Natural DE (Brand Name Celite-S) from Sigma Aldrich; AW-2=Acid Washed DE from Ep Minerals (Reno, Nev.).

FIG. 24 shows that calcination and acid washing decreased DE's affinity for exosomes. A single first void clean catch urine sample was split into 5 ml aliquots in 15 ml polypropylene tubes and exposed to 300 ul of a slurry (1 g into 10 mls of PBS) of different grades of Diatomaceous Earth acquired from several sources (see FIG. 23 Description). The mixture was incubated at RT for 20 minutes, then the DE was removed from the mixture by a 3 minute 1500×g spin (supernatant poured off). The treated DE was washed 2× by 5 mls of PBS then suspended in 150 ul of Laemmli buffer. 50 ul of this was run on SDS PAGE gel and transferred to Nitrocellulose. The Nitrocellulose was probed with Mabs specific for extra-cellular vesicle markers CD9 and Rab5. Shown are signals from Rab5 and CD9 as judged by MW and important properties (if known) of each grade of DE.

FIG. 25 shows Perlite (Sil-Kleer) with smaller pore sizes/ permeability can also isolate Extra-cellular Vesicles SilKleer is the commercial name for a type of Perlite which is volcanic glass heated to expand and form pores. It contains less $SiO_2$ than DE. Methods: A single first void clean catch urine sample was split into 5 ml aliquots in 15 ml polypropylene tubes and exposed to 300 ul of a slurry (1 g into 10 mls of PBS) of different grades of Diatomaceous Earth or Perlite acquired from several sources (see below). The mixture was rocked slowly for 20 minutes then the DE was removed from the mixture by a 3 minute 1500×g spin (supernatant poured off). The treated DE was washed 2× by 5 mls of PBS then suspended in 150 ul of Laemmli buffer. 50 ul of this was run on SDS PAGE gel and transferred to Nitrocellulose. The Nitrocellulose was probed with Mabs specific for extra-cellular vesicle markers CD9 and Aquaporin 2. Shown are signals from glycosylated Aquaporin-2 and Rab5 as judged by MW and important properties (if known) of each grade of DE. Grades and sources of Diatomaceous Earth:=Natural Food Grade DE from PermaGuard; 17-S=#17-S grade Perlite(Sil-Kleer) from Silbrico Corp (Hodgkins, Ill.); 23-S=#23-S grade Perlite(Sil-Kleer) from Silbrico Corp (Hodgkins, Ill.); 27-M=#23-S grade Perlite (Sil-Kleer) from Silbrico Corp (Hodgkins, Ill.).

Figure 26:
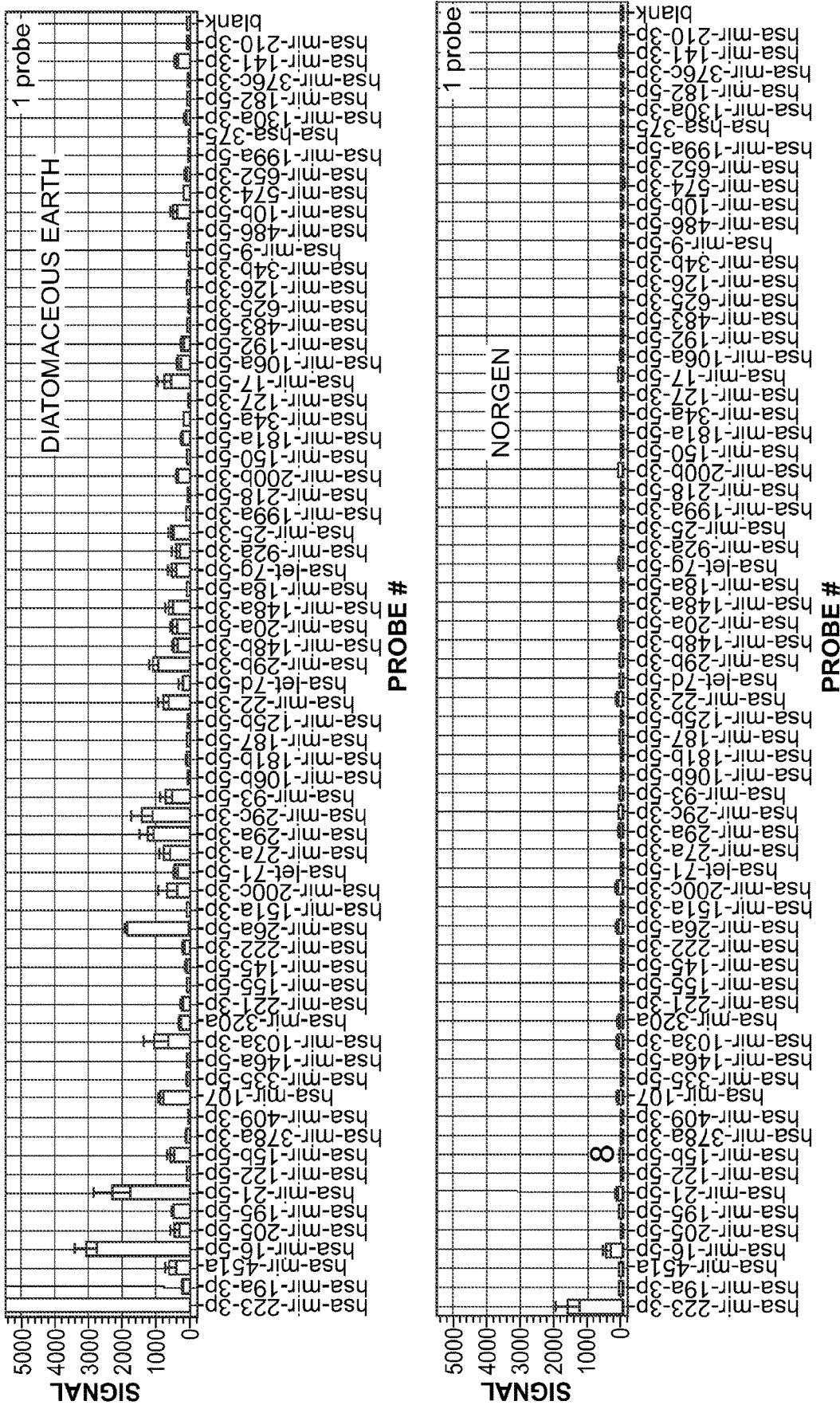

FIG. 26 shows that Diatomaceous Earth (DE) purified complex RNA. Diatomaceous Earth-purified microRNA was more complex than Norgen kit: RNA from identical 30 ml samples was isolated via DE or Norgen kit and analyzed for microRNA level with Firefly miRNA Array Panel as per FIG. 8.

Figure 27:
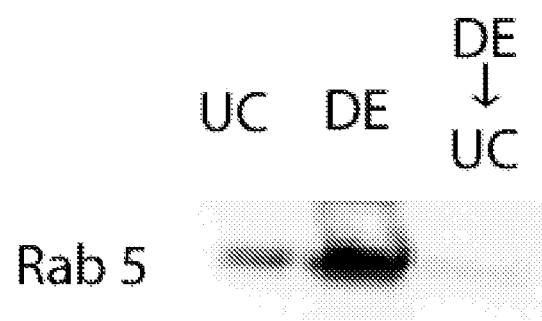

FIG. 27 shows that Diatomaceous Earth (DE) isolated exosomes from cell culture media. Jurkat Cells were grown for 24 hours in DMEM media plus 5% Fetal Bovine Serum. Cells and debris were spun out of 2 mls of the media for 10 minutes at 1500×g. The resulting cell free media was split in two and subjected to a Diatomaceous Earth protocol (see FIG. 21) or an Ultracentrifugation protocol (see FIG. 10). Furthermore, the bioparticle-depleted supernatant from the DE protocol was saved and subjected to the ultracentrifugation protocol. The pellets from all three procedures were suspended in Laemmli buffer, and half of that suspension was loaded on an SDS PAGE gel, and was then transferred to Nitrocellulose and was probed with a monoclonal antibody (Mab) specific for vesicle marker Rab5. Lane 1; Ultracentrifuge isolated vesicles. Lane 2; DE isolated vesicles. Lane 3; DE treatment almost completely depleted cell culture media of vesicle-derived Rab5.

DETAILED DESCRIPTION OF THE INVENTION

The present invention provides compositions and methods for producing preparations of isolated secreted microvesicles, RNA, DNA and protein-nucleic acid complexes (collectively called "bioparticles") from a liquid sample. The invention also provides methods for producing biofluids and blood serum/plasma that has been at least partially depleted of bioparticles. These methods have a number of advantages over the state of the art, which will be apparent from the discussion herein.

In certain aspects, the instant invention provides methods for the isolation of bioparticles (including, e.g., microvesicles, exosomes, etc.) from a liquid sample (e.g., a biofluid of a subject or cell culture). Kits for performance of such isolation steps, and instructions for their use, are also provided.

I. Definitions

As used herein, the term "bioparticle" refers to cell-free, membraned structures secreted from mammalian cells such as but not limited to microvesicles, exosomes, apoptotic bodies, LDL-particles etc., plus cell-free, relatively stable, protein-nucleic complexes secreted from mammalian cells such as but not limited to microRNA-AGO2 complexes, plus cell-free DNA (cfDNA) and cell-free messenger RNA. Thus, certain exemplary bioparticles include cell free miRNA (depicted), proteins, lipids, glycoproteins, DNA, mRNA, tRNA, other types of RNA, etc., which can exist relatively stably outside of cells, in various forms, including but not limited to: protein-nucleic acid complexes, exosomes, microvesicles, LDL particles, and apoptotic bodies.

As used in this application, the term "cells" encompasses not only eukaryotic cells, e.g., higher eukaryotic cells such as mammalian cells, as in human cells or mouse cells, but also prokaryotic cells, such as eubacteria cells and Archaea cells.

As used herein, the term "microvesicle" refers generally to any plasma membrane bound particle that may reside within the cell, or in the extracellular environment. These structures are not limited in any way with regard to in vivo localization (e.g., intracellular or extracellular), in a body fluid, in a cell culture media, generated by in vitro cultured cells, mechanism of origin or size characteristics. In some embodiments, a microvesicle can range in size with a lower size limit of at least about 20 nanometers (nm) in diameter, or alternatively, 30 nm, or 40 nm, or 50 nm in diameter. In some embodiments, a microvesicle has an upper size limit of not more than about 1,000 nm (i.e., 1.0 micrometer, micron, or μm), or alternatively, not more than about 1,500 nm, about 2,000 nm or about 2,500 nm. As used herein, the term "secreted microvesicle" is used synonymously with "circulating microvesicle (cMV)" or "extracellular microvesicle (emV)" or "extracellular vesicle (eV)" and refers to a subset of microvesicles that are found in an extracellular space under normal physiological conditions. As used herein, it is not intended that the term "circulating microvesicles" to be limited to microvesicles of any particular size or size range, or any particular production mechanism. For example, but not limited to, a cMV of the invention can be produced by (i) exocytosis from multivesicular bodies to produce exosomes, (ii) budding, fission and shedding of microvesicles directly from a cytoplasmic membrane, and (iii) membranous blebs caused by programmed cell death leading to the formation of apoptotic bodies. As used herein, the term "cMV" is not limited to microvesicles of any particular size or size range.

Although mechanistic theories for the endogenous production of circulating microvesicles are found in the scientific literature, any knowledge of such mechanisms is not required to make or used the present invention. It is not intended that the term "circulating microvesicles" as used herein be limited in any way with regard to the mechanism of their in vivo production.

As used herein, the term "shedding microvesicle (SMV)" refers to a class of microvesicles that are produced by cells using a mechanism of direct plasma membrane budding, fission and shedding to produce microvesicles that are released by a cell into an extracellular environment. As used herein, it is not intended that an SMV of the invention be limited by any particular size or size range.

As used herein, the term "exosome" refers to a subset of circulating microvesicles that are preformed microvesicles that are released from the cell following the exocytic fusion of intracellular multivesicular bodies with the plasma membrane, i.e., exosomes have an endocytic origin. As used herein, it is not intended that an exosome of the invention be limited by any particular size or size range.

As used herein, the term "crystal/precipitation-inducing agent" refers to an agent capable of promoting crystal formation and/or precipitation in a liquid sample. Exemplary "crystal/precipitation-inducing agents" of the invention include monosodium urate, uric acid, a salt thereof and a combination thereof.

As used herein, the term "apoptotic body" refers to a subset of circulating microvesicles that are produced as a result of apoptotic cell destruction. As used herein, it is not intended that an apoptotic body of the invention be limited by any particular size or size range.

As used herein, the term "isolating," or "to isolate," refers to any artificial (i.e., not naturally occurring) process for treating a starting material, where the process results in a more useful form of a molecule or structure of interest that is in the starting material. The "more useful form" of the molecule or structure of interest can be characterized in a variety of ways, no one of which is limiting. For example, as used herein, the invention provides methods for isolating secreted microvesicles from conditioned cell culture media. Further, for example, the process for isolating can result in:

(i) the molecule of interest having a greater concentration in the isolated form compared to the starting material (e.g., concentrating), (ii) the removal of any amount or any type of impurities from the starting material (e.g., purifying), (iii) an increase in the ratio of the amount of molecule of interest to the amount of any undesired component in the starting material (e.g., enriching), (iv) any artificial process for removing a molecule or structure of interest from its natural source or location;

(v) any artificial process for separating a molecule or structure of interest from at least one other component with which it is normally associated (e.g., purifying), or (vi) any combination of (i), (ii), (iii), (iv) or (v).

Similarly, as used herein, the term "isolated" generally refers to the state of the molecule or structure of interest after the starting material has been subjected to a method for isolating the molecule of interest. That is to say, isolating a molecule of interest from a starting material will produce an isolated molecule. For example, the methods of the invention are used to produce preparations of isolated microvesicles. These preparations of microvesicles have been isolated from their natural source, for example, from urine, or from conditioned cell culture media.

As used herein, the term "purifying" or "to purify" a molecule or structure of interest refers to a process for removing at least one impurity or contaminant from a starting material. For example, purifying a molecule of interest from a starting material refers to a process for removing at least one impurity from the starting material to produce a relatively more pure form of the molecule of interest.

As used herein, the term "substantially purified" refers to molecules or structures of interest that are removed from their natural environment or from a starting material (i.e., they are isolated) and where they are largely free from other components with which they are naturally associated or substantially free of other components that may render future use or study sub-optimal, difficult or impossible.

As used herein, the terms "purified" or "partially purified" refers to molecules or structures of interest that are removed from either (1) their natural environment, or from (2) a starting material (i.e., they are isolated), and where (a) at least one impurity from the starting material has been removed, or (b) at least one component with which the molecule is naturally associated has been removed. A "purified" or "partially purified" molecule may still contain additional components that may render future use or study of the molecule sub-optimal, difficult or impossible.

As used herein, the term "enriching" (and "enriched" and the like) refers to a process whereby a molecule of interest that is in a mixture has an increased ratio of the amount of that molecule to the amount of other undesired components in that mixture after the enriching process as compared to before the enriching process.

As used herein, the term "concentrating" refers to a process whereby a molecule of interest that is in a mixture that has been subjected to that process has a greater concentration after the process as compared to the concentration of the molecule in the mixture before the process.

As used herein, the term "depleted" refers to a mixture containing an undesirable component, where that undesirable component has been (i) completely removed from the mixture, (ii) sufficiently removed from the mixture to be undetectable, or (iii) partially removed from the mixture such that its concentration in the mixture is significantly reduced. For example, a blood serum that has been depleted of endogenous microvesicles may contain no microvesicles, or may contain no detectable microvesicles, or may contain a reduced level of microvesicles compared to the untreated serum.

As used herein, the expression "cell culture media" refers to any growth media that can support in vitro cell growth of a designated cell line. Such media can be supplemented or non-supplemented, for example, with 10% by volume, heat-inactivated fetal calf serum.

As used herein, the expression "minimal defined cell culture media" or "minimal media" refers to any culture media where each component is defined by name and the concentration of each component is known. Minimal defined cell culture media generally does not contain a serum supplement. For example, Dulbecco's Modified Eagle's medium (DMEM) is a defined minimal cell culture media. Minimal defined cell culture media generally can be used to culture cells in vitro, but not for extended periods of time.

As used herein, the expression "complete cell culture media" refers to a culture media that comprises a defined minimal cell culture media, and in addition, also comprises a complex supplement that enhances the growth properties of the culture media. For example, a blood serum supplement is commonly added to a minimal media to produce a complete cell culture media. Fetal calf serum (FBS or KS) is a common supplement (10% by volume) that is added to a minimal media to produce a complete culture media. Complete culture media are used to culture cells in vitro for indefinite (long) periods of time. As used herein, the expression "conditioned cell culture media" refers to any cell culture media (including complete media or minimal media) that has been exposed to live cells in culture. Conditioned cell culture media comprises not only the defined components of the minimal media and the serum supplement, but also contains additional components that the living cultured cells have produced. In many cases, conditioned cell culture media is a serum-free media.

Microvesicles

The term "microvesicles" (also known as microparticles) refers to a heterogeneous in vivo collection of membrane bound (i.e., encapsulated) biological structures. These structures are formed from lipid bilayer, which is the same lipid bilayer that comprises eukaryotic cell membranes. Microvesicles can reside within the cell, or in the extracellular environment. Microvesicle structures (intracellular and/or extracellular) are produced by nearly all mammalian cell types, as well as during in vitro cell culture.

The molecular composition of microvesicles is diverse, containing and/or transporting a variety of nucleic acids, proteins and lipids. Microvesicle molecular composition is generally reflective of the plasma membrane and antigenic content of the cell types, tissues and organs from which they originate, Mathivanan and Simpson, "Exosomes: extracellular organelles important in intercellular communication," J. Proteomics 73(10):1907-1920 (2010). Although protein composition of the microvesicles varies, most of these structures are enriched for various soluble protein markers, including HSP70, Hsc70, CD63, CD9, CD81 and others. Circulating microvesicles have also been reported to contain nucleic acids, including messenger RNAs, DNAs, and relatively high levels of small RNAs and microRNAs.

Circulating microvesicles are associated with numerous cell functions, including intercellular (cell-to-cell) communication, removal of metabolic byproducts and toxins (including misfolded proteins, cytotoxic agents and metabolic waste), angiogenesis, tissue regeneration, endocytic recycling of the plasma membrane, selective removal of plasma membrane proteins and regulation of immune functions such as antigen presentation. Some microvesicles have been shown to transport messenger RNA (mRNA) and micro-RNA (miRNA), which is highly suggestive of microvesicles functioning as messengers that allow one cell type to regulate the activity of a distant cell type by acting as a shuttle that can merge with the distant cell and release its contents into that target recipient cell. This microvesicle shuttle can utilize the body fluids to travel to distant sites and control the activity of distant target cells.

Circulating microvesicles (cMVs), or synonymously, extracellular microvesicles (eMVs) or extracellular vesicles (eVs), describe an eclectic group of microvesicles that are released by cells, and therefore, exist in extracellular spaces and/or reside in body fluids. The mammalian body fluids that are known or suspected to contain cMVs include, but are not limited to, blood, urine, saliva, breast milk, tears, sweat, ascites fluid and cerebrospinal fluid. Secreted microvesicles are also found in cell culture media that has been exposed to cultured mammalian cells.

With regard to defining and categorizing the cMV molecules that can be found in body fluids, there is lack of consensus as to the nomenclature and description of the different types of cMV particles. Some literature distinguishes at least three subcategories of circulating microvesicles, based on their mechanistic origin. The molecular/cellular mechanisms that produce microvesicles are theorized to include (i) exocytosis of intracellular multivesicular bodies, (ii) outward budding, fission and shedding of plasma membrane, and (iii) byproducts of apoptosis. The diverse collection of circulating microvesicle structures can range in size from about 20 nanometers (nm) to upwards of about 1,000 nm (i.e., 1.0 micrometer, micron, or μηπ) in diameter.

The first recognized subgroup of cMVs are those produced by direct plasma membrane budding, fission and shedding. Some sources describe these shed microvesicles as generally large, namely with lower sizes limits of at least 100 nm or 200 nm, and with an upper size limit of about 1,000 nm in diameter. Some have proposed that these structures be termed "ectosomes" or "shedding microvesicles (SMVs)." Still other groups state that ectosome particles may be as small as 40 or 50 nm in diameter.

A second recognized subgroup of cMVs are exosomes, that is, the preformed microvesicles that are released from the cell following the exocytic fusion of intracellular multivesicular bodies with the plasma membrane. These exosome structures are generally smaller than ectosomes, and have an upper size limit estimated to be about 100, 150 or 200 nm, and a lower size limit of about 40 nm or 50 nm. However, various sources differ in their size-based definitions for exosomes, and this size distinction remains unresolved.

A third group of structures is the apoptotic blebs released by dying cells. These membrane structures have a less well-defined size range, and may be anywhere from about 50 nm to about 5,000 run in diameter.

A unified microvesicle nomenclature and classification system utilizing broadly accepted definitions has been elusive in the field. In the literature, microvesicles have been alternatively referred to as microparticles, nanoparticles, exosomes, ectosomes, epididimosomes, argosomes, exosome-like vesicles, promininosomes, prostasomes, dexosomes, texosomes, archeosomes, oncosomes, exosome-like vesicles, apoptotic blebs, extracellular vesicles and shedding microvesicles. In some publications, uses of these terms is conflicting or overlapping. Simpson and Mathivanan (2012), "Extracellular Microvesicles: The Need for Internationally Recognized Nomenclature and Stringent Purification Criteria". J Proteomics Bioinform (2). doi:10.4172/jpb.l0000el0. One source suggests that a preferred nomenclature for circulating microvesicle is based on the microvesicle's mechanism of origin. Namely, these categories would be (i) the ectosomes produced by membrane budding, (ii) the exosomes produced by the exocytosis to intracellular multivesicular bodies, and (iii) the membrane blebs produced by the process of apoptosis.

The release of exosomes was highlighted from different cell types in a variety of physiological contexts. Thus, it has been shown that B cells release exosomes bearing molecules of the major histocompatibility complex class II, which play a role in antigen presentation (Raposo et al., *J. Exp. Med.* 183 (1996) 1161). Similarly, it has been shown that dendritic cells produce exosomes (also referred dexosomes) with specific structural and functional characteristics, and playing a role in mediating the immune response, including the stimulation of cytotoxic T lymphocytes (Zitvogel et al., *Nature Medicine* 4 (1998) 594). It has also been shown that tumor cells secrete in a controlled manner, specific exosomes (also designated texosomes) bearing tumor antigens and are able to present these antigens or to transmit them to antigen-presenting cells. It is also known that mast cells accumulate molecules in intracellular vesicular compartments, which can be secreted in response to signals (Smith and Weis, *Immunology Today* 17 (1996) 60). In general, it seems that the cells emit signals and communicate with each other through membrane vesicles they release, which may carry antigenic patterns, MHC molecules, or any other signal (cytokine, growth factor, etc.) which have special structural and functional characteristics and are produced in different physiological situations.

II. Methods for Isolating Bioparticles

The present invention provides methods for the isolation of bioparticles from liquid samples. In certain embodiments, the liquid sample is urine. From urine as an example, certain methods of the invention comprise the following steps:

A) (Optional) Preparing a Whole Urine Prespin Treatment Solution (also called Solution 1)

The purpose of the Whole Urine Prespin Treatment Solution is to reduce the amount of bioparticles lost in the first spin (prespin), which is typically performed to reduce the amount of cells and debris in the Whole Urine sample.

It is well known in the field that spinning urine at speeds above 17,000×g can lead to the loss of microvesicles due to the trapping action of the protein THP (also called uromodulin). However, it was discovered that a large amount of microvesicles could also be lost in the lower speed spins (below even 3000×g) that are typically used to remove cells and debris (see FIG. 20).

In certain embodiments, the Whole Urine Prespin Treatment Solution consists of the reducing agent TCEP. TCEP is preferred over DTT for this purpose, as it is active in a broader range of pH. In one embodiment, the concentration of the TCEP in the 10× solution would be at a concentration of 160 mM. Other embodiments have the TCEP 10× concentration being between 80 mM and 300 mM. Other embodiments use other reducing agents such as DTT at similar concentrations.

In other embodiments, the Whole Urine Prespin Treatment Solution consists of an acid buffer plus reducing agent such that addition of the acid buffer-containing Whole Urine Prespin Treatment Solution reduces the pH of the Whole Urine below 6.

In other embodiments where the reducing agent is not used, the Whole Urine Prespin Treatment Solution consists of a basic buffer that increases the pH of the Whole Urine to above 7 as it was discovered that without reducing agent present, less bioparticles are lost if the pH of the sample is above 7.

B) (Optional) Adding the Whole Urine Prespin Treatment Solution to the whole urine sample.

In certain embodiments, a $\frac{1}{10}^{th}$ volume of a 10× Whole Urine Prespin Treatment Solution is added to the whole urine sample to create a mixture. In other embodiments any combination of Prespin Treatment Solution and Urine Sample yielding a mixture with a final concentration of the TCEP or other reducing agent of from 5 mM to 30 mM and a pH below 6 is acceptable or, if no reducing agent is used, a pH above 7. No incubation is necessary; the next step can be taken immediately.

C) Centrifuging the Mixture

The mixture is subjected to a centrifugation. The centrifugation typically forms a pellet and a supernatant, although pelleted material may not be visible to the eye. In contrast to the prior art, this centrifugation does not require ultracentrifugation, e.g., does not require centrifugal forces in excess of 100,000×g. This centrifugation can be done at slower speeds, for example, to generate RCF values of not more than 30,000×g, or not more than 20,000×g, or not more than 12,000×g, or not more than 10,000×g, or not more than 5,000×g, or not more than 2,000×g, or not more than 1,500×g. In one embodiment, a centrifugation producing 1,000×g is used. The length of time for centrifugation is not limiting. In one embodiment, the centrifugation is for 5 minutes. Alternatively, the centrifugation can proceed for one or more minutes, two or more minutes, three or more minutes, four or more minutes, six or more minutes, seven or more minutes, eight or more minutes, nine or more minutes, ten or more minutes, fifteen or more minutes, twenty or more minutes, etc.

D) Removing the Supernatant

Following the spin, the resulting supernatant is carefully removed so as not to disturb the pellet, and the pellet is discarded.

E) Combining the Urine Supernatant from D) with the Crystallization/Precipitation Solution (Also Called Solution 2)

To initiate the crystallization/precipitation of bioparticles, Solution 2 (see below) is added to the Supernatant generated in step D) to create a mixture. In one embodiment, a $\frac{1}{10}^{th}$ volume of a 10× concentration of Solution 2 is added to the supernatant, however, any combination that yields a 0.5× to 5× final concentration of Solution 2 in the mixture is acceptable.

F) Incubating the Resulting Mixture

The resulting mixture is then incubated. The incubation can be with any degree of cooling, for example at 5° C., although such cooling is not always required. The incubation times can vary, and are not in any way limiting. For example, incubation can be anywhere between 0 minutes to overnight (e.g., 16 hours). The incubation can be with or without mixing, and the mixing during the incubation period can be constant or intermittent. In certain embodiments a 15-minute incubation on ice is performed.

G) Centrifuging the Mixture

The mixture from F) is subjected to a centrifugation. The centrifugation typically forms a pellet and a supernatant, although pelleted material may not be visible to the eye. In contrast to the prior art, this centrifugation does not require ultracentrifugation, e.g., does not require centrifugal forces in excess of 100,000×g. This centrifugation can be done at slower speeds, for example, to generate RCF values of not more than 30,000×g, or not more than 20,000×g, or not more than 12,000×g, or not more than 10,000×g, or not more than 5,000×g, or not more than 2,000×g, or not more than 1,500×g. In the one embodiment, a centrifugation producing 2,000×g is performed. The length of time for centrifugation is not limiting. In one embodiment, the centrifugation is for 5 minutes.

H) Removing the Supernatant

Following the spin, the resulting supernatant is carefully removed so not to disturb the pellet, and this supernatant is discarded.

I) Resuspending the Pelleted Material

After removal of the supernatant, the pellet is resuspended in any desired resuspension solution and collected for further analysis. The resuspension solution can use either water, phosphate buffered saline (PBS), or any other suitable aqueous, such as any isotonic solution. In some embodiments, the resuspension solution is basic in nature, for example, 100 mM Tris pH 8. The volume used for the resuspension is most typically the smallest possible practical volume, and is typically many times smaller than the volume of the original liquid sample comprising the secreted microvesicles. In some embodiments, the volume of the resuspension solution is smaller by at least one order of magnitude than the volume of the original liquid sample.

III. Liquid Samples

The present invention provides methods for isolating circulating bioparticles from liquid samples. It is not intended that the nature of the liquid samples be in any way limited, and can be any liquid sample that contains bioparticles. Advantageously, very small volumes of liquid sample can be used, for example, as little as about 10 µL, 50 µL, 0.1 mL, 0.2 mL, 0.3 mL, 0.4 mL, 0.5 mL, 1.0 mL, or 2.0 mL. or 3.0 mL. or 5.0 mL of starting sample can be used.

In some embodiments, the liquid sample can be conditioned cell culture media that has been used to culture a cell line in vitro that has produced bioparticles, and therefore, those bioparticles are now contained in the conditioned media. The conditioned cell culture media can be a complete media (containing a serum supplement), or a serum-free culture media.

In some embodiments where the conditioned cell culture media is a complete media comprising a serum supplement, the serum supplement that is used can be a serum that has been depleted of any endogenous circulating bioparticles prior to addition of the supplement to the defined minimal growth media. The present invention also provides methods for producing such bioparticle-depleted serum.

In some embodiments, the liquid sample is a biofluid (synonymous with body fluid). The body fluid that is used in the analysis is not particularly limited. Bioparticles can be isolated from any body fluid using the methods of the invention, even though a particular body fluid is not itemized herein, as it is intended that the present methods find use with any and all body fluids. For example, body fluids that can be analyzed by the methods of the invention include, but are not limited to, amniotic fluid, blood serum, blood plasma, breast milk, cerebrospinal fluid, lymph, mucus (including nasal drainage and phlegm), pericardial fluid, peritoneal fluid, semen, synovial fluid, tears, urine, sweat, saliva, and ascites fluid.

IV. Crystallization/Precipitation Reagents (Solution 2)

The present invention provides methods for the isolation of bioparticles from liquid samples, where the methods use a crystallization/precipitation solution (Solution 2), combined with the liquid sample, to initiate the bioparticles precipitation and isolation. Certain embodiments use Monosodium Urate in solid form, slurry form, or liquid form (solubilized in a basic solution such as NaOH). Another embodiment uses Uric Acid. Another embodiment uses some other salt of Uric acid. The amount used depends on the sample volume. One embodiment uses from 1 to 100 nM Monosodium Urate. Optionally, a Monosodium Urate or other crystallization/precipitation reagent at a concentration of 1, 2, 3, 4, 5, 10, 20, 30, 40, 50, 60, 70, 80, 90 or 100 nM can be added to a sample in an amount of 5 µL, 10 µL, 20 µL, 30 µL, 40 µL, 50 µL, 60 µL, 70 µL, 80 µL, 90 µL, or 100 µL or more, to promote a crystallization/precipitation event in the sample. It was discovered that Uric Acid and optionally Monosodium Urate when added to a liquid, optionally urine, crystallizes and/or induces a precipitate that includes bioparticles but excludes many proteins and salts contained in the liquid.

V. Matrix Reagents (Solution 2)

The present invention provides methods and compositions for isolating bioparticles that, without wishing to be bound by theory, appear to exploit pore sizes of certain materials to effect bioparticle enrichment, such as the pore sizes found in porous beads, such as siliceous beads or particles, examples of which include diatomaceous earth (DE) and perlite. In certain embodiments, the porous beads (e.g., porous siliceous beads) are non-calcinated, non-acid washed, (i.e. natural grades) diatomaceous earth with average pore sizes ranging from 0.1 to 10 microns and permeabilities less than 2 darcies. In some embodiments, the porous beads (e.g., porous siliceous beads) are Perlite (i.e. treated volcanic glass) with pore sizes from 0.1 to 10 microns and permeabilities less than 2 darcies. It is contemplated that matrix reagents with average pore sizes in the range of 0.01 micron to 50 microns, including in the range of 0.01 to 1 micron, 0.5 to 40 microns, 0.5 to 50 microns, 1 to 20 microns, 1 to 10 microns, 2 to 5 microns, and/or about 3, 4, and/or 5 microns are effective reagents for isolation of microvesicles/bioparticles as described herein. Similarly, it is contemplated that agents with permeabilities of less than 5 darcies, less than 2 darcies, less than 1 darcy, less than 0.5 darcies, less than 0.3 darcies, or smaller can be effective reagents for the methods and compositions of the invention. Exemplary grades of DE are non-calcinated, non-acid washed, "natural" forms possessing pore sizes between 0.5-2 microns in diameter and permeability below 0.1 Darcies (FIGS. 23-24). Certain exemplary Perlite grades have a permeability below 3 and pore sizes below 10 microns (FIG. 25).

EXAMPLES

The following examples are offered to illustrate, but not limit, the claimed invention.

It is understood that various modifications of minor nature or substitutions with substantially similar reagents or components will be recognizable to persons skilled in the and these modifications or substitutions are intended to be included within the spirit and purview of this application and within the scope of the appended claims.

Figure 1:
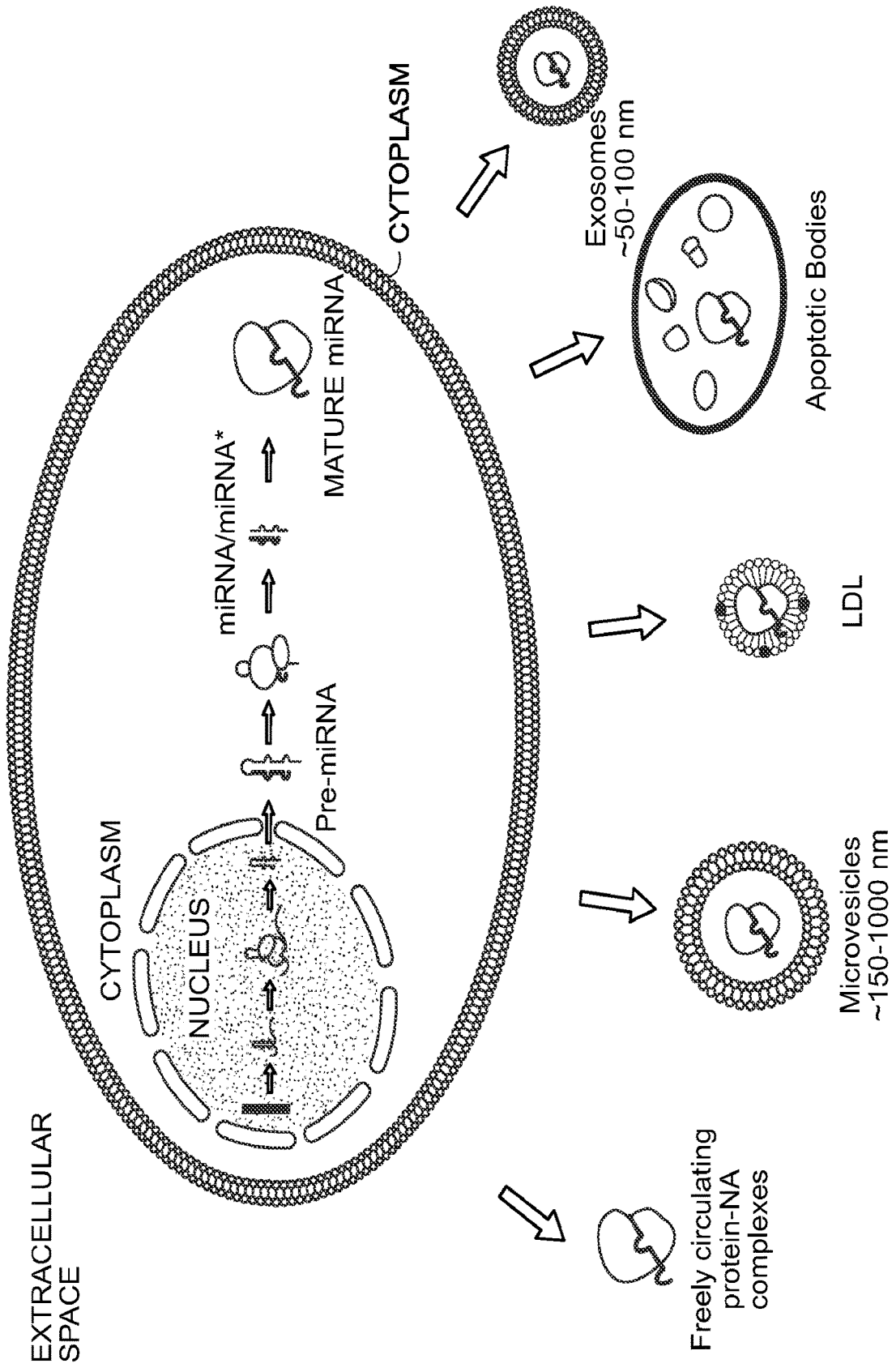
FIG. 1 shows an exemplary range of biomarkers from cells such as miRNA (depicted), proteins, lipids, glycoproteins, DNA, mRNA, tRNA, etc., which can relatively stably exist outside of cells in various forms, including but not limited to: protein-nucleic acid complexes, exosomes, microvesicles, LDL particles, and apoptotic bodies.

Cell-free membrane and/or protein-containing structures found in urine have high value as biomarkers for disease or disorder diagnosis, and even for approaches involving screening of urine for therapeutic targets (e.g., biomarker and/or targetable miRNAs). Cell-free biomarkers are preferred agents to work with because they are relatively easy to isolate, are less variable in content/consistency than whole cells and/or whole cell-containing fluids, and can travel from the tissue of their origin into easy to isolate biofluids, such as urine (FIG. 1).

A number of methods have been implemented and/or proposed for isolating microvesicles (Ms) from urine; however, all have significant limitations (FIGS. 2-3). In particular, current methods other than those described herein—both commercial and non-commercial—possess one or more of the following drawbacks:

1. Certain methods require expensive equipment (e.g., ultracentrifuge methods);
2. Certain methods require expensive kits (e.g, NEP, Qiagen, Exiqon);
3. Certain methods are difficult to scale up (e.g., Norgen (only a 1 ml column), ultrafiltration filters (e.g., Amicon) can clog
4. Many such methods are time consuming (e.g., ultracentrifuge methods, SBI, Lifetech, Exiqon);
5. Certain methods produce low yield, especially from certain fluids, such as urine (e.g., NEP, SBI, Lifetech, Exiqon);
6. Certain methods use phenol (e.g.,Lifetech).

An unmet need was thus identified for isolation of bioparticles (e.g., microvesicles, exosomes, etc.) from urine, as well as other bodily fluids (e.g., saliva, as well as blood, plasma, etc.). The instant methods were newly identified to allow for rapid and inexpensive isolation of extracellular membrane particles, including microvesicles, exosomes and apoptotic bodies. The methods described herein were also observed to isolate membrane-free protein-nucleic acid particles as well. Finally, obtaining intact bioparticles is an advantage of the current invention, with such bioparticles used in mechanistic, vaccine- and delivery-related and therapeutic studies.

One advantage of certain of the currently described methods is that they use common laboratory reagents and apparatuses, and do not require high-speed centrifugation (e.g., use of an ultracentrifuge). Thus, the current methods are designed to achieve a higher yield than previously available methods, also allowing for isolation of important biomarkers and/or therapeutic targets from a smaller volume of sample than could be obtained using previously described approaches.

Development of Novel Systems for Isolation of Circulating Bioparticles

Being unsatisfied with current methods for the isolation of circulating bioparticles, including exosomes, from urine and other biofluids, the following experiments were initiated and undertaken in an effort to develop new and improved methods for this purpose.

It was known that urine contains several constituents (chemicals) that can be present at saturating concentrations and thus can form crystals in vivo and in vitro and also can be easily precipitated from a urine sample in vitro. Since it was also known that certain crystals can form on and/or interact with epithelial cell membranes in the urinary tract, it was hypothesized, since microvesicles are membrane structures as well, that crystal growth on microvesicles could be induced artificially and then the microvesicle-crystal complex could be easily centrifuged out of solution as a method for microvesicle purification. Similarly, it was noticed while working with urine that the same group of endogenous chemicals present at near saturation levels, often spontaneously precipitated in vitro when exposed to lower temperatures and/or artificial concentration. It was hypothesized that artificially increasing the levels of some of these constituents could reliably induce a precipitate that would include bioparticles. It was also realized that the addition of these constituents of the urine approach to other liquids containing bioparticles (e.g., saliva, blood, plasma, etc.) would similarly crystallize/precipitate bioparticles (as was demonstrated in Example 3 below).

After an extensive trial and error process that examined different constituents of urine, it was discovered in certain embodiments that the addition of Monosodium Urate, but also optionally (additionally and/or alternatively) Uric Acid, or other salts of Uric Acid could indeed induce a crystallization/precipitation of urine and that the resulting sediment of this included biomarkers known to be present in microvesicles and cell-free protein-nucleic acid complexes.

Example 1

A Newly Discovered Na Urate Protocol Isolated Microvesicles from Urine Quickly and Effectively To exemplify certain methods of the invention, 3 mls whole urine samples from two different donors (one sample was naturally concentrated and one sample was naturally dilute) were treated with 16 mM TCEP reducing agent as part of a Whole Urine Prespin Treatment Solution, which simultaneously reduced the pH to <6 and was believed to have reduced the matrix-forming properties of the abundant endogenous urine protein, THP. The mixture was immediately centrifuged at 1,000×g for 5 minutes to remove cells and debris. The supernatant was gently removed and then 40 microliters per ml of sample of 131 mM Monosodium urate (in 1 N NaOH) was added to create a mixture. This mixture was incubated for 15 minutes on ice and then centrifuged for 5 minutes at 1,000×g in a desktop microcentrifuge. After centrifugation, the supernatant was gently removed and the pellet was resuspended in a small volume of PBS buffer.

At the same time, using the same samples, bioparticles were isolated using the gold standard method of Ultracentrifugation using a published protocol (Fernandez-Llama Tamm-Horsfall Protein and Urinary Exosome Isolation (2010) Kidney Int. 77:736-742), as well as with three commercial precipitation kits (SBI, Life Technologies, and Exiqon), following their protocols. The instant method took 25 minutes, as compared to 2.5 hours for ultracentrifuge, 14 hours for SBI, 2 hours for Exiqon and 3 hours for Life Technologies. The instant method required no special equipment, while the Ultracentrifuge method requires a ~$35,000 ultracentrifuge and rotor. The commercial methods all required an expenditure of between ~$2 to ~$10, while the instant method required approximately 1 penny worth of Monosodium urate.

Figure 4:
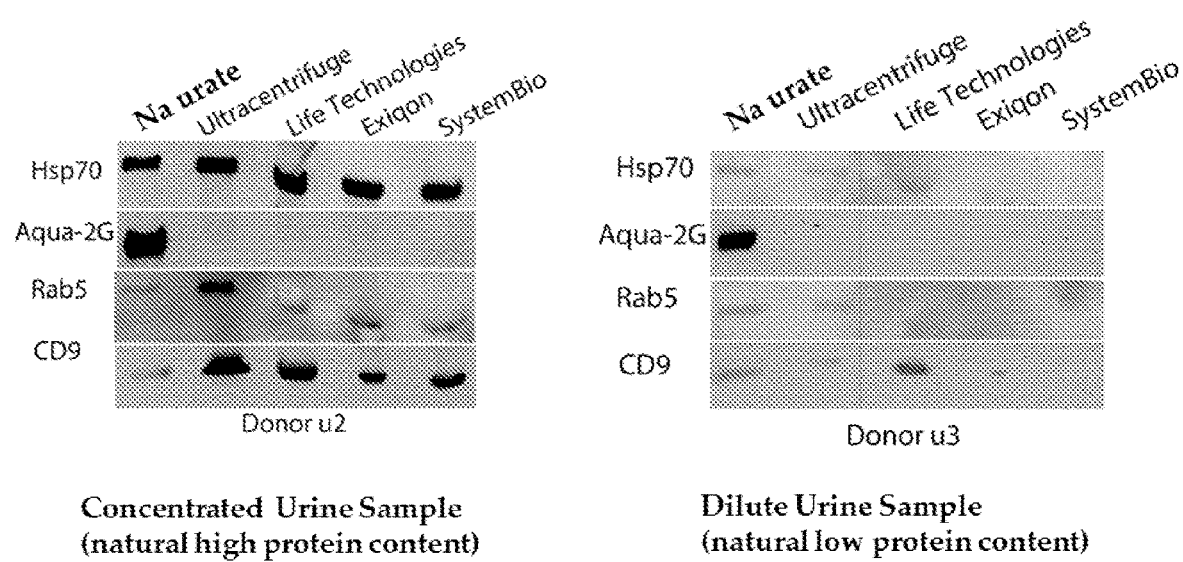
FIG. 4 shows that a Na Urate bioparticle isolation protocol of the invention worked more consistently than ultracentrifugation or any of three different commercial kits. Unlike other methods, Na urate isolated vesicle markers, even from dilute samples. Methods: Two 15 ml samples; 1 naturally concentrated (left panel) and 1 naturally dilute (right panel) were split into 5 equal parts and were subjected to the Na Urate protocol (see Example 1), ultracentrifugation, or one of three commercial urine exosome isolation kits (from Life Technologies, Exiqon, and System Bio, respectively). Following each procedure, equal amounts of the final pellet were loaded onto SDS page and subjected to western blot analysis using antibodies specific for known microvesicle protein markers HSP70, Aquaporin 2, Rab5 and CD9. Only the Na Urate protocol isolated all four markers from both samples. As a control, vesicles were also isolated by ultracentrifugation (2000×g 10 min spin, followed by a 17,000×g 10 min spin, followed by a 100,000×g spin for 1 hour); vesicles were isolated using the following commercial kits as per their instructions: miCURY Exosome Isolation Kit (Exiqon, Woburn, Mass.), ExoQuik-TC, (SBI, Mountain View, Calif.) and Total Exosome Isolation Reagent (Life Technologies, Carlsbad, Calif.).

Protein biomarkers for microvesicles were assayed for all of the above preparations. As shown in FIG. 4 (which presents the results of multiple western blots using antibodies specific for four protein biomarkers), all 5 methods were able to isolate HSP70, Rab5, and CD9 from the more concentrated sample (left panel); however, the instant method isolated significantly more of the urine-specific vesicle marker Aquaporin-2G than the other methods. As for the more dilute sample, only the instant method isolated all four microvesicle markers (right panel). The commercial kits from Exiqon and Systems Bio were unable to isolate significant amounts of any of the biomarkers from the naturally dilute sample.

Figure 5:
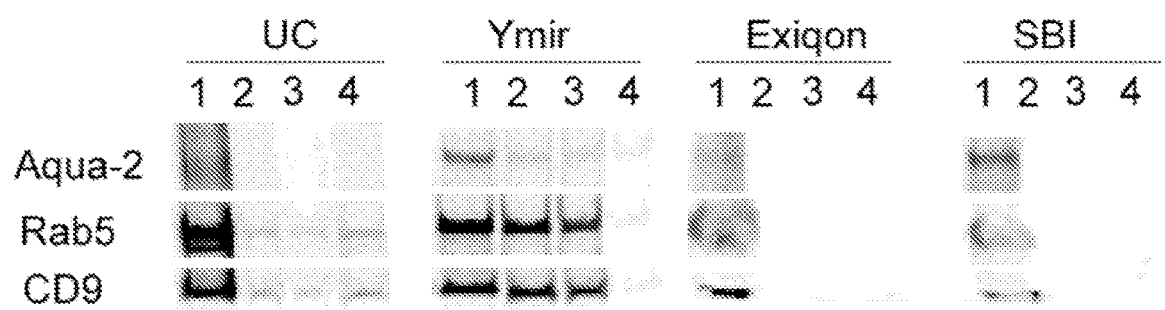
FIG. 5 shows that Na Urate functioned even in very dilute samples. Methods: A 12 ml first void clean catch urine sample was split into four equal parts and subjected to Na Urate ("Ymir"), ultracentrifugation ("UC"), miCURY Exosome Isolation Kit ("Exiqon", Exiqon Woburn, Mass.), or ExoQuik-TC, ("SBI", SBI Mountain View, Calif.). The Na Urate prep was performed as per Example 1. Ultracentrifugation was performed as per FIG. 4. The commercial kits were performed as per manufacturer instructions. The resulting preps were subjected to immunoblot analysis with Mabs for vesicle markers Aquaporin 2, Rab5, and CD9. The full strength preps are shown in lane 1 of each panel. The same sample was also diluted 2×, 4×, and 8× (lanes 2, 3, and 4, respectively, for each panel) with PBS before being subjected to the same prep methods.

To ascertain if the instant method was consistently superior to other methods for more dilute urine samples, the instant method, UC, and commercial kits obtained from Exiqon and SBI were applied to 3 mls of a single concentrated sample, or to the same sample diluted with PBS 2×, 4×, or 8×. As shown in FIG. 5, only the instant method (second panel from the left) was able to isolate the biomarkers Aquaporin 2, Rab5 and CD9 from the 4× diluted sample. In contrast, the two commercial methods were unable to isolate any significant biomarkers from the 2× diluted samples. Given the wide range of concentrations of urine samples and given that some diseases or conditions such as alcoholism, diabetes, and kidney disease can cause a substantial dilution or concentration of urine, the instant Na Urate methods' ability to isolate extra-cellular vesicles from a wide range of urine concentrations provided a substantial advantage over any and all art-recognized methods examined. By any criteria; cost, time, or consistency of yield, the instant method was superior to all of these methods for isolating protein biomarkers associated with microvesicles.

Figure 6:
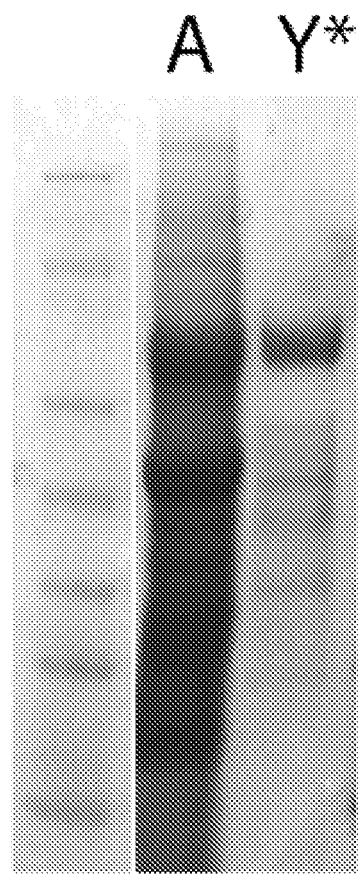
FIG. 6 shows that the Na Urate protocol precipitated a subset of the total extra-cellular protein and thus could be considered a "purification". "A" corresponds to Amicon preparation, while "Y*" corresponds to the Na Urate protocol of certain aspects of the invention. Method: A single 6 ml first void clean catch urine sample was split in two and either concentrated with an Amicon protein purification column (3000 MW cut-off) or subjected to the Na Urate bioparticle isolation protocol of certain aspects of the invention. Equal amounts (by volume) of each processed sample was loaded onto an SDS PAGE gel and subjected to Coomassie protein stain. Significantly less protein was seen in the bioparticle isolation prep (Y*), as compared to total protein from the Amicon column (A).

To determine if the instant method was indeed purifying bioparticles from urine, that is, if there was less protein in the instant method prep than in the starting sample, a urine sample was split in two with half of the sample concentrated by an Amicon protein purification column (Ultra-15; ultracel-3K) and the instant method applied to the other half. Equivalent amounts of the resulting preps were loaded onto a SDS PAGE gel and the protein on the gel was stained with Coomassie stain. FIG. 6 shows that there was substantially less total protein in instant method prep (Y*) than in the Amicon prep. Thus, the instant method concentrated protein markers for microvesicles while removing other proteins from urine. Because the Na Urate method of the invention precipitated a subset of the total extra-cellular protein, the method was identified as a true purification method.

Figures 7A, 7B, 7C:
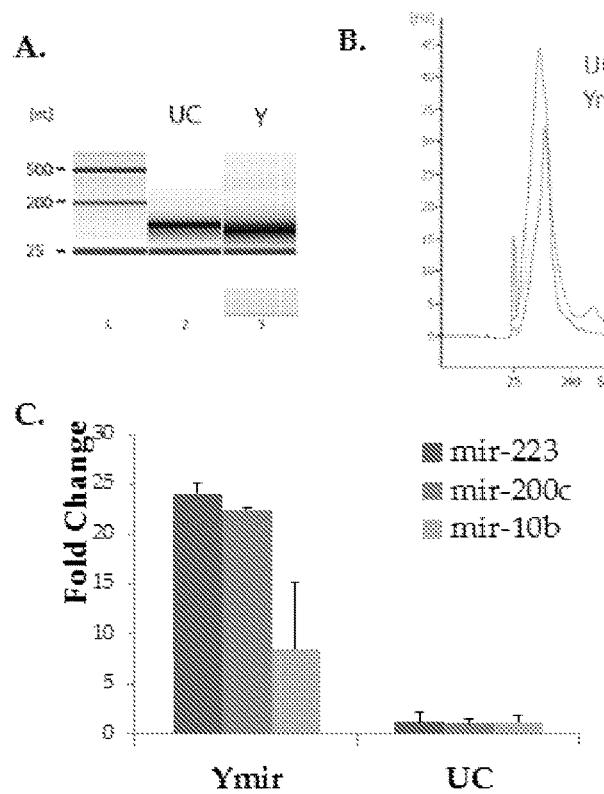
FIGS. 7A to 7C shows that the Na Urate process isolated high quality RNA, especially miRNA.
Figure 8:
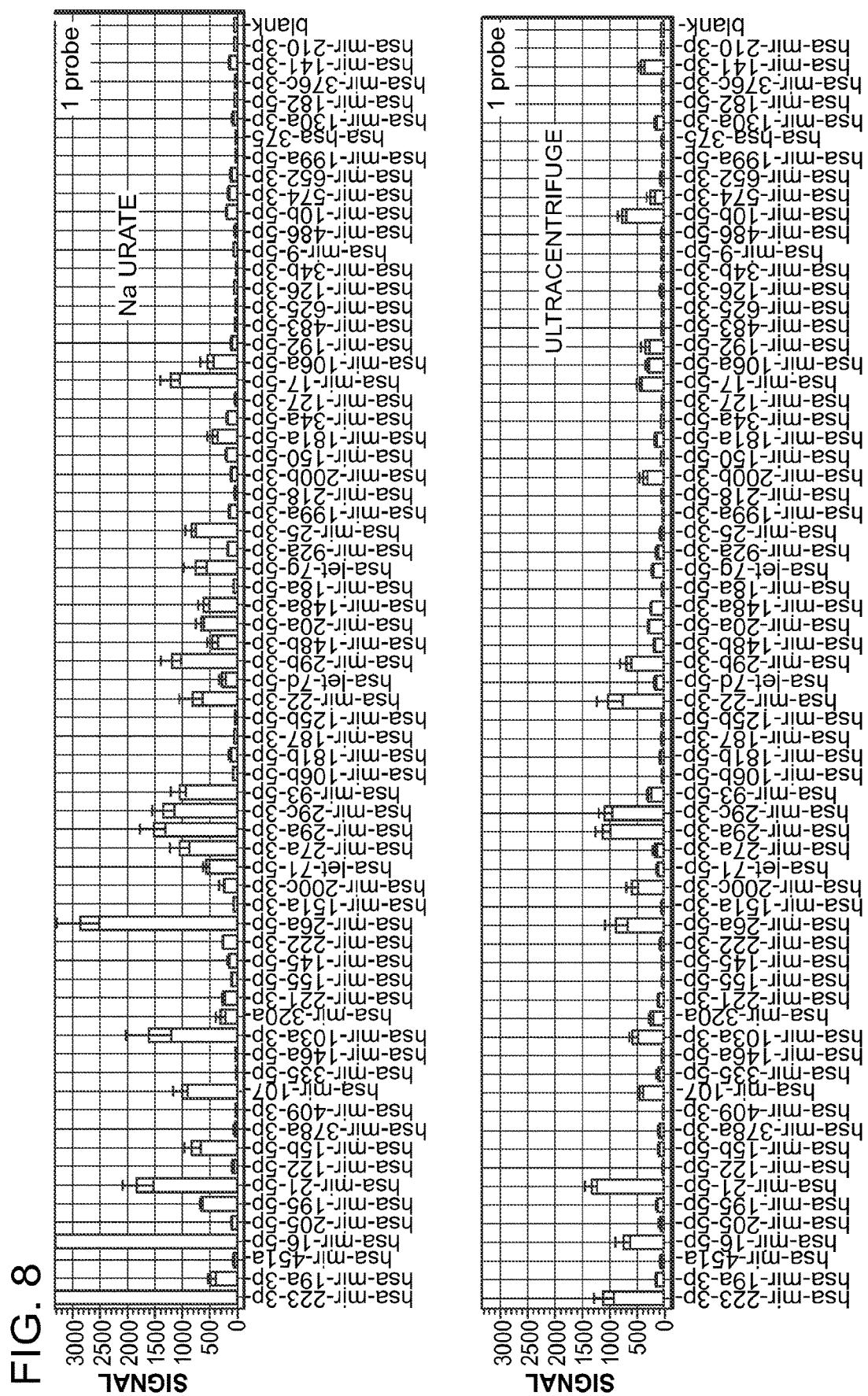
FIG. 8 shows that Na Urate purified complex RNA, including miRNAs. Indeed, Na Urate purified miRNA was more complex than Ultracentrifuge-purified MiRNA. RNA from identical samples was isolated via Na Urate or Ultracentrifuge methods and analyzed for microRNA level(s) with Firefly miRNA Array Panel (Abeam Cambridge Mass.).

To assess the quality of biomarkers isolated by the newly-identified Na Urate process, isolated RNA from such preparations was examined, particularly miRNA. As shown in FIGS. 7A to 7C, in which the Na Urate process of the invention (labeled "Y" in FIG. 7A) was compared to an ultracentrifuge (UC) process for the isolation of RNA from 10 ml of urine, high quality RNAs of all types were obtained. The instant method specifically produced an amount of RNA equivalent to that produced by the ultracentrifuge method, as judged by RNA Bioanalyzer (FIGS. 7A and 7B). As shown in FIG. 7C, the instant method isolated from 8-24× more of 3 miRNAs than ultracentrifugation (UC), as assessed by quantitative RT-PCR. To determine if this was true for microRNAs in general, 69 respective microRNA levels were assayed via Firefly microRNA array. in samples obtained via UC or the instant method FIG. 8 shows that a similar pattern of detected microRNAs was seen in both preps; however, the instant method yielded a significantly stronger signal for the majority of microRNAs. The fact that the instant method isolated similar amounts of total RNA but much more miRNA suggested that the instant method was isolating cell-free miRNA-protein complexes, as well as miRNAs contained in extracellular vesicles.

Figure 9:
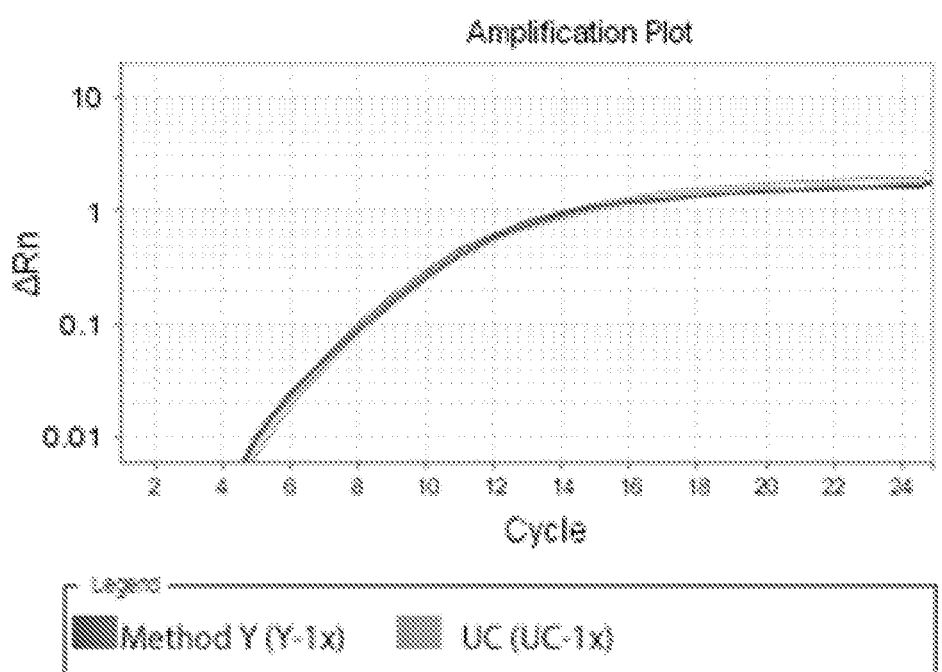
FIG. 9 shows that the Na Urate protocol isolates RNA without PCR inhibitors. One concern for RNA purification from biofluids, especially urine, was that Enzymatic inhibitors such as Urea will be co-purified; however, a known amount of cel-mir-39 (a non-human miRNA) was spiked into a UC prep and a Na Urate prep. The amount of cel-mir-39 detected was identical between the two preps, demonstrating that Na Urate did not purify more PCR inhibitors than Ultracentrifuge.

It was important for downstream analysis that a given method did not co-purify PCR inhibitors with the RNA. To test for this, isolated bioparticles prepped by the instant method or by ultracentrifuge were spiked with the non-endogenous microRNA cel-mir-39 from *C. elegans*, and then PCR was performed using probes specific for this microRNA. If the instant method introduced PCR inhibitors to a greater extent than the gold standard ultracentrifuge method, then a lower amount of cel-mir-39 would have been detected for the instant method as compared to ultracentrifuge. Since an identical amount of cel-mir-39 was detected in both methods, FIG. 9 shows that in the instant method, isolated RNA did not contain PCR inhibitors, as compared to ultracentrifuge preparations.

It was highly desirable to isolate whole microparticles, rather than just RNA or protein from microparticles. Whole microparticles can be used for functional experiments directed towards therapeutic discovery (De Toro et al. "Emerging roles of Exosomes in Normal and Pathological Conditions: New insights for Diagnosis and Therapeutic Applications. (2015) Front. Immunol. 6:203). They also can be used as a delivery agent for therapeutic and research payloads (Tran et al. "Exosomes as Nanocarriers for Immunotherapy of Cancer and Inflammatory Diseases. (2015) Clin Immunol. PMID: 25842185). To determine if the instant method isolated whole microparticles, Transmission Electron Microscope and a Nanosight nanoparticle tracking analysis (NTA) device were employed. The Nanosight device used lasers to visualize and track the Brownian motion of individual particles (Dragovic et al., "Sizing and phenotyping of cellular vesicles using Nanoparticle Tracking Analysis," Nanomedicine: Nanotechnology, Biology and Medicine (2011), doi:10.1016/j.nano.2011.04.003). This allowed for obtainment of precise size and concentration data for the isolated microparticles.

Figure 10:
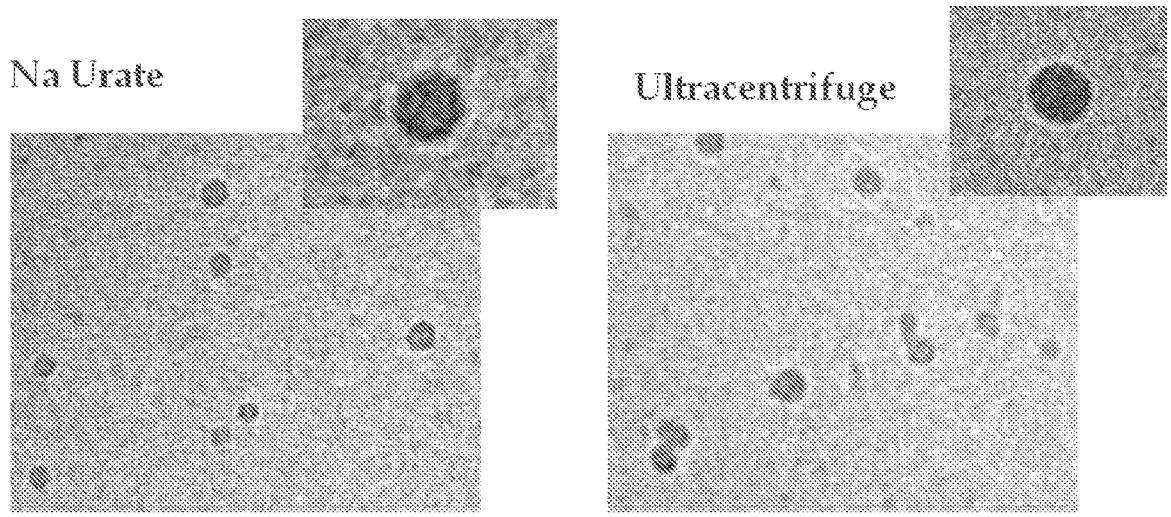
FIG. 10 shows transmission electron microscopy (TEM) images that demonstrate that Na Urate isolated whole exosomes, when used as described herein. A 4 ml sample of first void clean catch urine was split in two. Half was subjected to Na Urate precipitation/crystallization (Method Y, left panel; see example 1) and half was subjected to standard ultracentrifugation. Both methods yielded particles of similar sizes and shapes as judged by transmission electron microscopy. Vesicles were also isolated by ultracentrifugation as follows: urine sample was sequentially centrifuged for 10 min at 2,000×g and at 17,000×g for 10 min to remove cells and cellular debris then the resulting supernatant was centrifuged at 200,000×g for 60 min at 24 C to sediment exosomes.

If the instant method degraded or altered the microparticles significantly, then the size and/or shape of the vesicles would have been predicted to appear different when compared to UC isolated vesicles by Transmission Electron Microscopy. FIG. 10 shows that that was not the case, as the populations of vesicles obtained using each method were essentially indistinguishable for size and shape. Similarly, the NTA traces from the different preparations would have been expected to show fewer particles and/or differently sized particles, were there a significant difference in the quality of the respective preparations. As shown in FIG. 11, the instant method isolated a similar number of particles as the ultracentrifuge method. Furthermore, the size distribution of those particles obtained using the Na Urate method was nearly identical in comparing between the two methods. These results for the instant method strongly suggested that the instant method isolated whole exosome and microvesicle particles that closely approximated the gold standard isolation method of ultracentrifuge.

Figure 12:
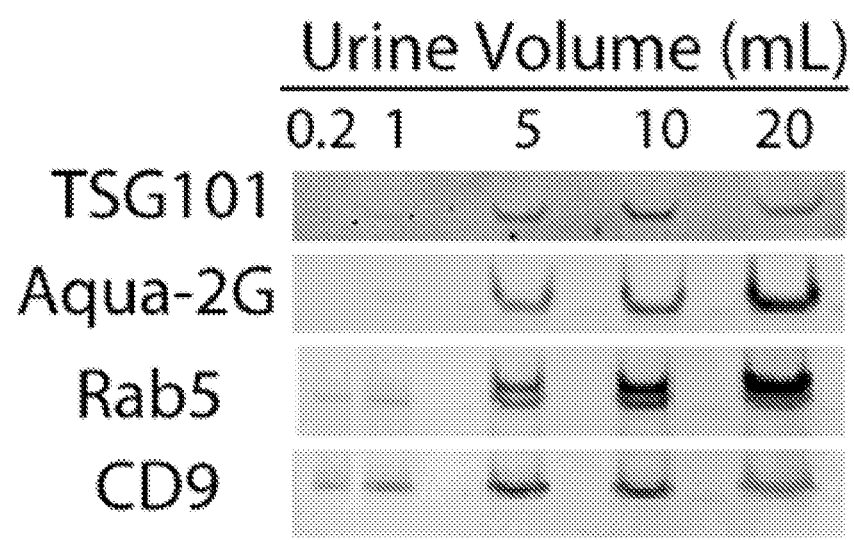
FIG. 12 shows that the Na Urate protocol was scalable (protein). An immunoblot of the instant method (see example 1) from different amounts (indicated) of a single first void clean catch urine sample using Mabs specific for vesicle markers TSG101, Aquaporin 2, Rab 5 and CD9.
Figure 13B:
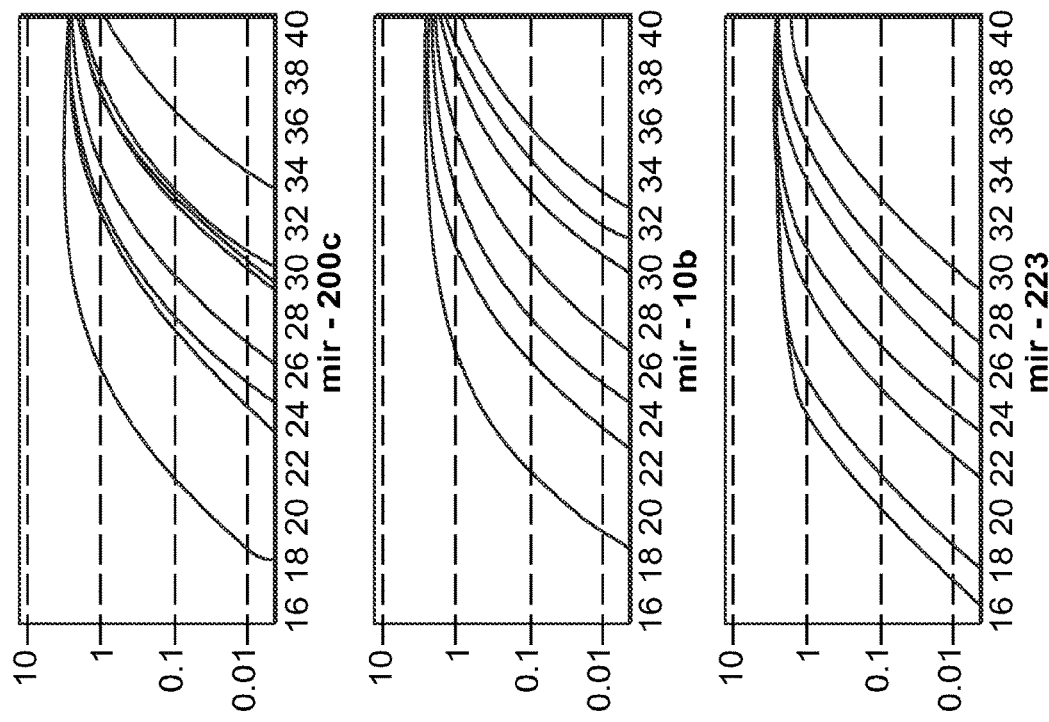
FIGS. 13A and 13B show that the Na Urate protocol was scalable (RNA). An qRT-PCR values for 3 miRNAs isolated from different amounts (indicated) of the same first void clean catch using the Na Urate protocol (example x). qRT-PCR traces used to calculate Ct values shown in FIG. 13A. The lower the Ct value the higher the concentration. Methods: RNA isolation and qRT-PCR as per FIG. 12.
Figure 13A:
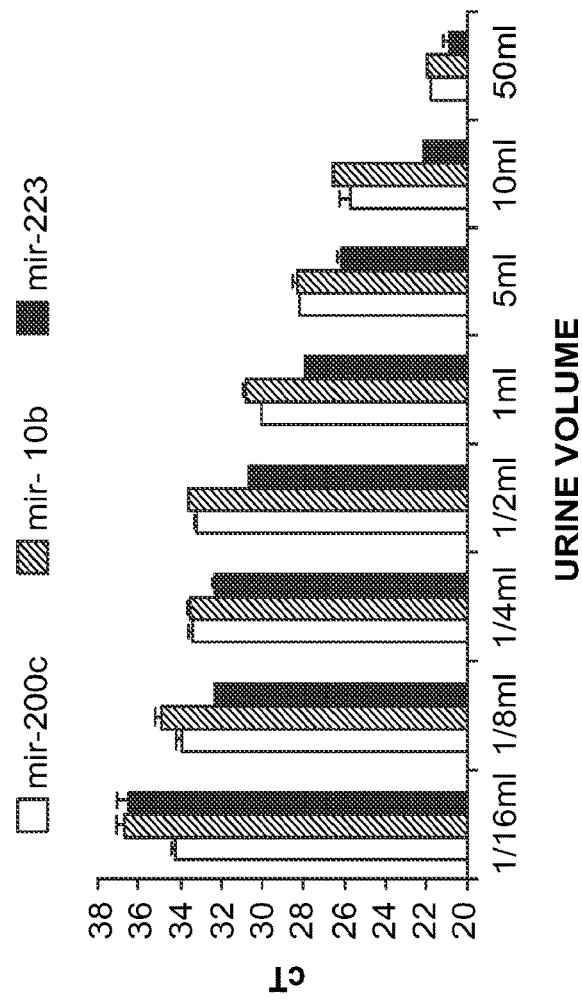

One of the drawbacks of isolating bioparticles using Ultracentrifugation, binding columns, and/or sieving columns is that there are substantial labor and expense costs when scaling up to larger volumes (i.e. many more ultracentrifugation runs and many more expensive columns are required for larger volumes, as each ultracentrifugation tube and column could only hold a small amount of sample). Therefore, it was of interest to determine if the instant method linearly scaled to larger volumes of urine for both protein and RNA bioparticle markers. FIG. 12 shows that scalability was an attribute of protein markers, and FIG. 13 shows this was true for microRNA markers.

Figure 14A:
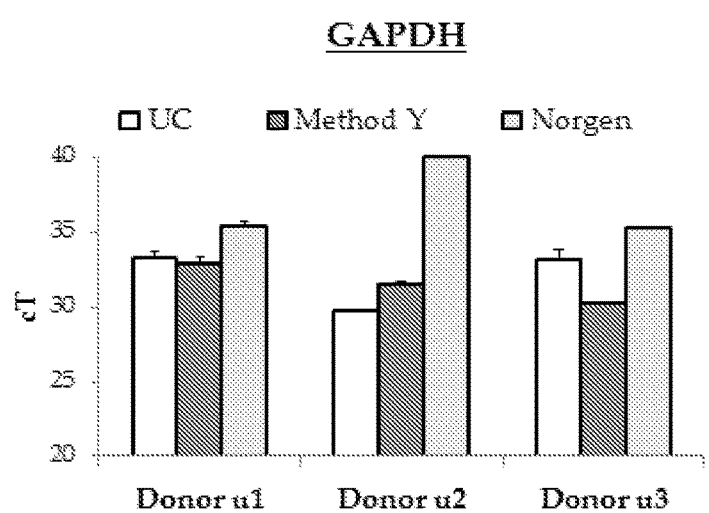
FIGS. 14A and 14B show that the Na Urate protocol could isolate extra-cellular mRNA. qRT-PCR values for GAPDH messenger RNA (mRNA) isolated from different first void clean catch urine samples from 3 donors using the Na Urate protocol (Method Y; example 1), ultracentrifugation (UC) and the Norgen Urine Exosomal RNA Kit. qRT-PCR traces used to calculate Ct values shown in A. Methods: RNA isolation as per FIG. 12, except that an extra 15 minute DNAse step was added at the end.
Figure 14B:
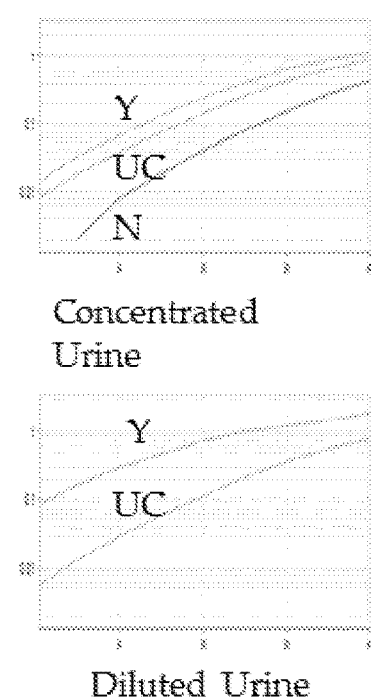

As shown in FIGS. 14A and 14B, the instant method isolated extra-cellular messenger RNA (mRNA) as well as or better than Ultracentrifugation or a commercial kit specific for RNA (obtained from Norgen).

Example 2

Figure 15:
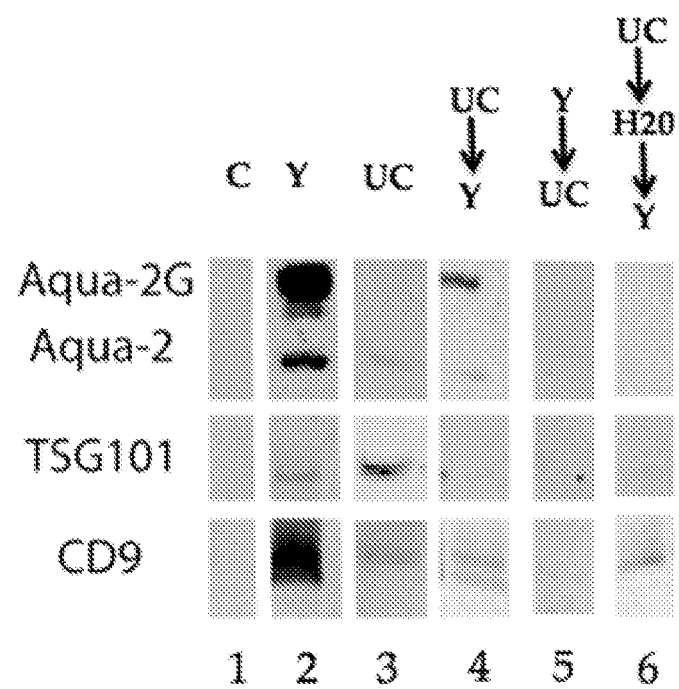
FIG. 15 shows that Na Urate isolated vesicles from UC-depleted urine supernatant and even from vesicles suspended in pure $H_2O$. The Na Urate ("Y") protocol isolated vesicles that ultracentrifugation ("UC") missed, whereas ultracentrifugation could not isolate vesicles from urine depleted of vesicles isolated by Na Urate. Furthermore, Na Urate was even capable of isolating a small amount of urine vesicles purified by ultracentrifugation and resuspended in pure H2O, suggesting that Na Urate could isolate vesicles from any fluid. Methods: 4.5 mls of first void clean catch urine was divided into three parts and subjected to either just a control double low speed spin (lane 1), the Na Urate protocol (example 1; lane 2) or ultracentrifugation (as per FIG. 4; lane 3). The vesicle depleted supernatants were saved and subjected to the reciprocal methods Na Urate (lane 4) or ultracentrifugation (lane 5). Separately, a 1.5 ml first void clean catch sample was subjected to ultracentrifugation. The vesicle pellet was washed 1× with PBS then resuspended in $H_2O$. The $H_2O$ plus vesicles was subjected to Na Urate, incubated, and spun as per FIG. 4 legend. Then analyzed by immunoblot with Mabs specific for Aquaporin 2, TSG101, and CD9.

The Na Urate Process More Completely Depleted Urine of Bioparticles than the Ultracentrifuge Method The fact that the instant Na Urate method isolated significantly more of several protein and microRNA markers for bioparticles, and also of particles as judged by NTA and TEM (see Example 1 above), strongly suggested that the instant method could isolate the same bioparticles which the heretofore gold standard method of ultracentrifugation could. This was important, as there was also value in depleting biofluids such as urine, blood serum/plasma, and tissue culture serum of bioparticles. To determine if the instant method more completely depleted urine of bioparticles than the ultracentrifuge method, the instant method and the ultracentrifuge method were applied to 1.5 mls of urine from the same sample. Subsequently, the respective final supernatants for each method represented bioparticle-depleted urine. These depleted urine samples were then applied to the alternate method (i.e. the instant method was applied to the ultracentrifuge supernatant and the ultracentrifuge method was applied to the instant method supernatant). FIG. 15 shows that, as in Example 1 above, the instant method final pellet yielded significantly more AQ2 and CD9 than the ultracentrifuge method did (lane 2 vs lane 3, respectively). Strikingly, application of the instant method to the ultracentrifuge method's depleted supernatant yielded a significant amount of AQ-2 and CD9 exosomal markers (lane 4), suggesting that the instant method isolated a significant amount of exosomes that the ultracentrifugation method missed. On the other hand, the ultracentrifugation method was incapable of isolating any detectable exosomal markers from the instant method's final supernatant (lane 5). These results demonstrated that the instant method was superior for generating urine depleted of exosomes.

Example 3

Figure 16:
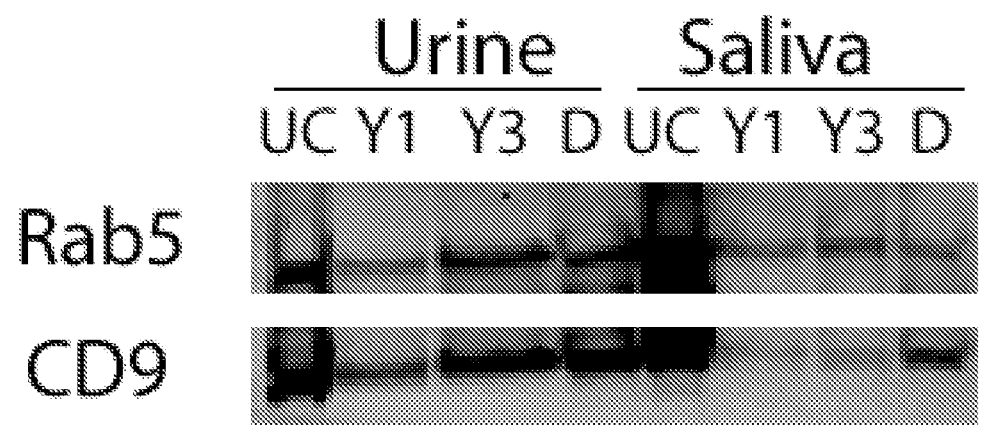
FIG. 16 shows that the Na Urate protocol isolated vesicle markers in saliva as well as urine. Methods: A first void clean catch urine sample was processed with Na Urate as per Example 1. A saliva sample was diluted 2× with PBS and then spun 2×1500 g to remove cells, cell debris, and mucous. Na Urate was added to 5 mM (40 ul of 0.131M stock/ml of sample) concentration and incubated on ice for 20 minutes before being spun at 1000 g for 5 minutes. The resulting pellet was resuspended in Laemmli buffer and run on PAGE along with the results for the urine prep. Immunoblot analysis was performed with Mabs specific for vesicle markers Rab5 and CD9. UC Ultracentrifugation protocol as per FIG. 4 with 3 mls of Urine or 5 mls of Saliva as indicated; Y1=The instant method on 1 ml of Urine or Saliva as indicated; Y3=The instant method on 3 mls of Urine or Saliva as indicated; D=200 ul slurry of Diatomaceous Earth as per Example 1 on 3 mls of Urine or Saliva as indicated.

The Na Urate Process Isolated Bioparticles/Microvesicles from Non-Urine Biofluids To determine if the instant method could isolate bioparticles from liquid other than urine, bioparticles were initially isolated from 1.5 ml of urine using ultracentrifuge. These bioparticles were then added to pure water, and the instant method was applied. This was considered to be an ideal test for the hypothesis that the instant method could isolate bioparticles from other fluids, because water contains no salt, has a neutral pH, and also has no other constituents of urine. As FIG. 15 shows, the instant method was capable of isolating a small amount of TSG101 and a significant amount of CD9 exosomal markers even from water (lane 6). Although little Aqua-2 was recovered, this was likely due to the small amount of Aqua-2 isolated by ultracentrifuge in the first place (lane 3), which meant that little Aqua-2 was introduced into the water at the outset. This demonstrated the ability of the instant method to isolate bioparticles from liquids other than urine. To demonstrate this ability of the instant method in a natural biofluid, the instant method was also applied to 1 ml and 3 mls of saliva. As shown in FIG. 16, the instant method (Y1 and Y3) was capable of isolating significant and dose-dependent amounts of extracellular vesicle markers Rab5 and CD9 from saliva.

Example 4

Figure 17:
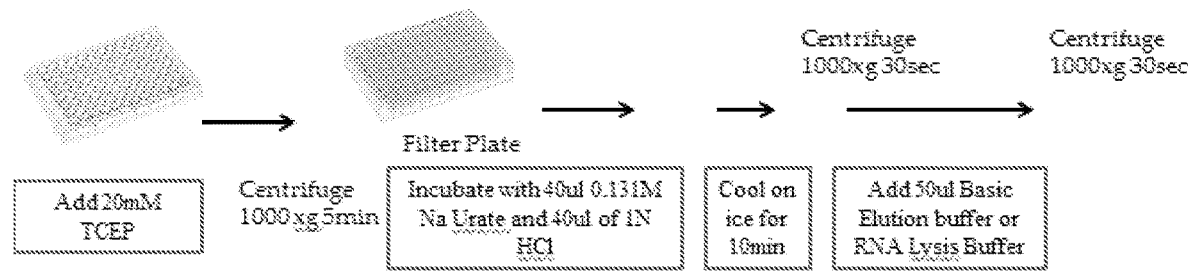
FIG. 17 shows the 96-well plate protocol for the Na Urate protocol. The protocol is one for using the Na Urate Protocol for small volumes in a 96 well format, suitable for automation.
Figure 18B:
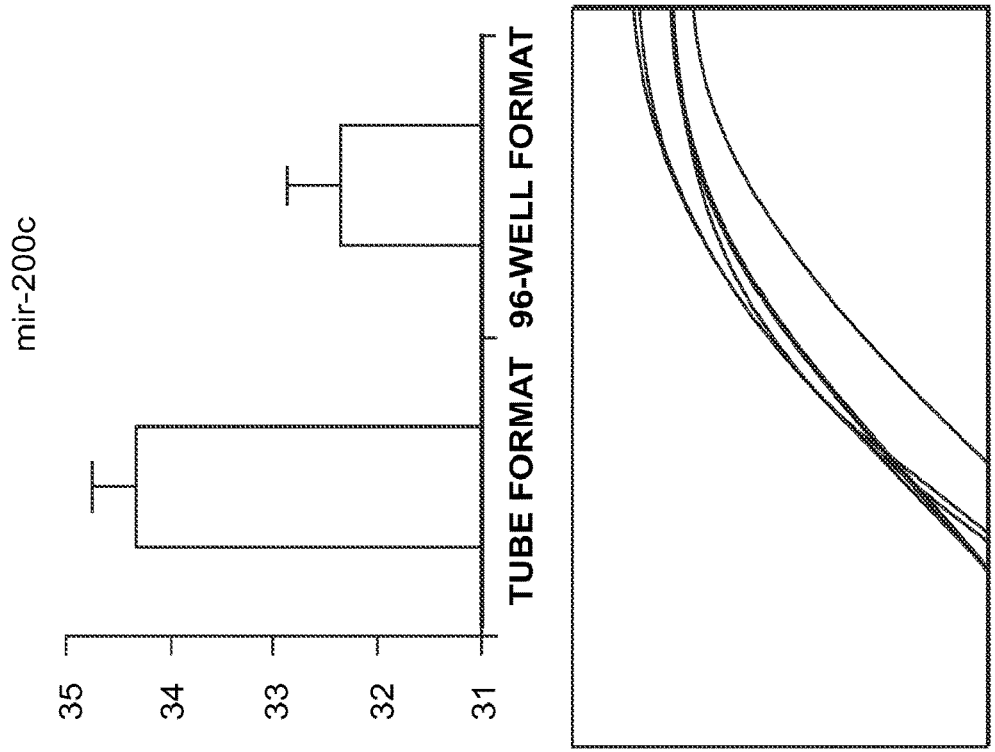
FIGS. 18A and 18B show 96-well plate data for the Na Urate protocol. The efficiency of the Na Urate protocol allowed for the isolation of measurable quantities for biomarkers from small volumes of sample. The simplicity of the Na Urate protocol allowed for the use of 96 well plates and semi-automation.
Figure 18A:
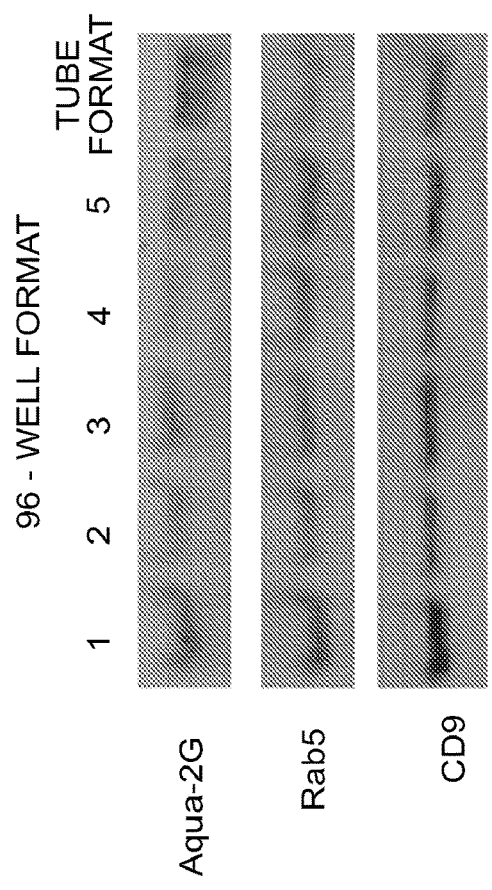

The Efficiency of the Na Urate Purification Methods of the Invention Enabled Use of 96 Well Format Plates for High-Throughput Bioparticle Isolation Given the ability of the methods of the instant invention to isolate significant amounts of extracellular vesicle markers from 1 ml and lower amounts of urine sample (See FIGS. 12 and 13A-13B) it became feasible, for the first time, to devise a bioparticle isolation protocol suitable for a 96-well plate format (1 ml and lower sample volumes). This was significant, as the ability to use 96-well plates allows for the automation of the method in a high-throughput manner, as there are many existing automation tools available for 96-well plates. FIG. 17 describes a 96-well plate protocol using TCEP and Sodium Urate and FIG. 18 shows that this protocol successfully isolated significant quantities of extracellular vesicle protein markers (FIG. 17A) and microRNA mir-200c (FIG. 17B) from only 200 ul of sample. Surprisingly, this format was significantly superior to the more standard tube format for isolating mir-200c (32 PCR Cts compared to 34 PCR Cts).

Example 5

Figure 19A:
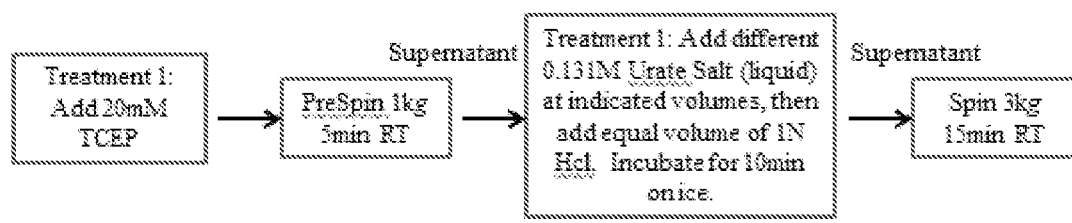
FIGS. 19A and 19B show that different Uric Acid salts work similarly in the Urate-based. EV isolation protocol. Protocol for experiment (as per example 1). Western blot analysis of vesicle protein isolated from a single 12 ml first void clean catch urine sample divided into 12 parts and treated with different amounts (as labeled in ul) of different Urate salts as labeled.
Figure 19B:
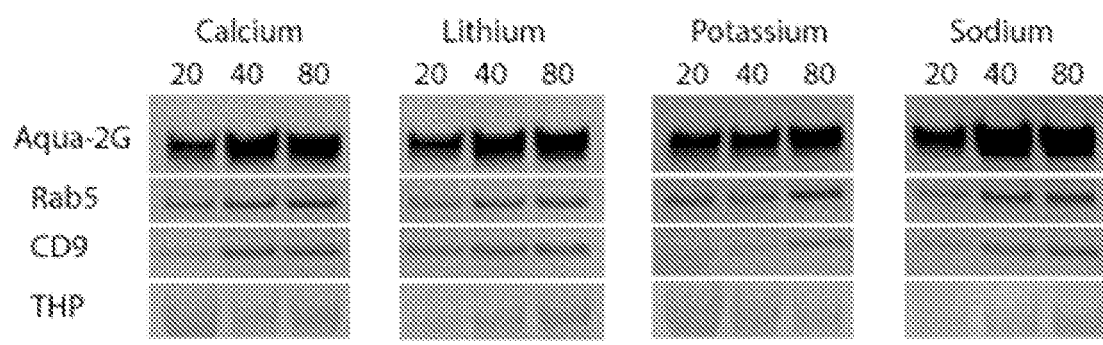

Alternative Urate/Uric Acid Compositions were Identified as Effective for Bioparticle Isolation from Urine and Other Biofluids While the above experiments were primarily performed using sodium urate (Na Urate) to promote biomarker/microvesicle isolation from urine, a range of uric acid salts also capable of isolating such biomarkers/microvesicles was also identified. As shown in FIGS. 19A and 19B, uric acid salts other than sodium (of Na Urate), specifically, Calcium, Lithium and Potassium, were also assayed for the ability to isolate bioparticles/microvesicles. Thus, many additional salts of the compounds of the invention were also identified as active in the methods of the invention.

Example 6

Figure 20:
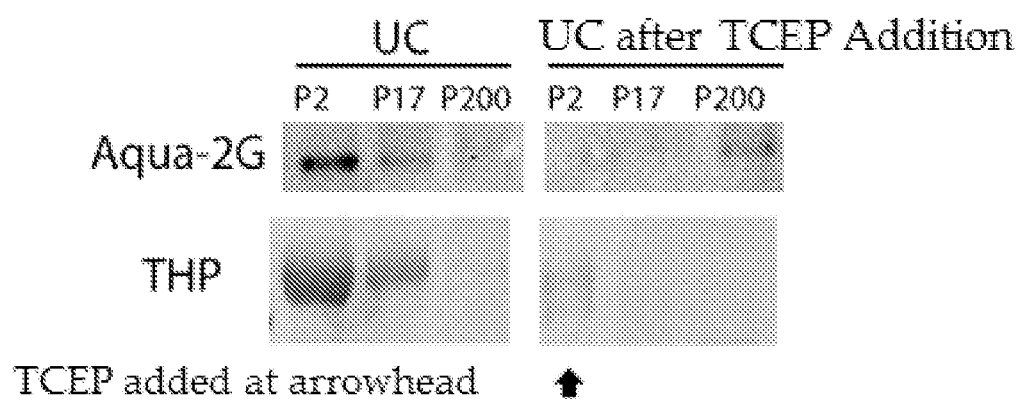
FIG. 20 shows that TCEP added to the urine before the first spin reduced EV loss. Adding TCEP to sample before the first spin was easier than the current art, where DTT is used to recover EVs from the first pellet and leads to decreased pelleting of Tamm-Horsefall Protein (THP) and exosomes and increased final yield. TCEP was preferable to DTT for this purpose because it has a wider range of pH activity (urine has a pH range from 4-8). Methods: immunoblot using a Mab specific for the urine vesicle marker Aqua-2G and protein stain showing THP of an experiment where extra-cellular vesicles were isolated using multiple centrifugal spins at indicated speeds either without (left panel) or with 16 mM (final concentration) of TCEP added to the urine sample. Adding TCEP reduces the amount of pelleted THP and EVs and increases the yield from the final 200,000×g pellet. P2=2000×g spin for 10 minutes; P17=17,000×g spin for 10 minutes; P200=200,000×g spin for 1 hour.

Diatomaceous Earth Isolated Vesicle Protein Markers from Urine, While Control Silica Did Not Following extensive searches for conditions that could exploit the association of large, matrix-forming proteins such as THP with exosomes for bioparticle purification, it was initially discovered that addition of the robust reducing agent TCEP within a pre-spin centrifugation of urine samples could allow for improved removal of whole cells in initial clearing spins from urine, while retaining exosomes within the supernatant of such spins (FIG. 20). It was additionally discovered that following such a pre-clearing spin performed with one goal of preventing formation of bioparticle-protein aggregates during such an initial clearing spin, bioparticle aggregation could then be promoted and used in favor of purification of bioparticles in a subsequent spin, via use of an agent capable of promoting bioparticle aggregation (see Example 1 and FIGS. 4-16). It was newly discovered that Diatomaceous Earth and certain other siliceous particles were surprisingly effective at promoting bioparticle association and aggregation, with both speed and at low cost, and with remarkably good yields from multiple biofluids (urine and saliva) of a widely representative number of bioparticle markers (FIGS. 21, 22). Indeed, the newly discovered methods of the invention accomplished yields of a remarkably broad RNA profile from urine or saliva (with speed and at exceedingly low cost, see FIGS. 21-23), as compared to prior art methods (e.g., Norgen). It was also observed that calcination and acid washing could decrease DE's affinity for exosomes (FIG. 24).

DE is characterized by a nanometer to micrometer-range pore sizes. To examine if non-DE porous materials (i.e., Perlite, which is volcanic glass heated to expand and form pores) were also capable of isolating biomarkers/microvesicles, such agents were examined within the methods of the invention. As shown in FIG. 25, Perlite (Sil-Kleer), which possesses slightly larger pore sizes/permeability than DE, could also isolate extracellular vesicles. The pore size of the Perlite inversely correlated with its ability to isolate extracellular vesicle markers.

The products of DE-directed bioparticle/microvesicle isolations were also examined for the integrity of RNA (i.e., miRNAs) within such preparations. As shown in FIG. 26, DE purified highly complex populations of RNA (e.g., miRNAs), as compared to Norgen kit isolations. As shown in FIG. 27, DE-directed bioparticle/microvesicle isolation approaches of the invention also were highly functional in isolating well as depleting) exosomal biomarkers from cell culture media.

Thus, a high speed, low cost and highly efficient method of isolating bioparticles from multiple biofluids was identified, representing a dramatic improvement over methods previously described in the art.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description.

The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Those skilled in the art will recognize, or be able to ascertain using no more than routine experimentation, many equivalents to the specific embodiments of the invention described herein. Such equivalents are intended to be encompassed by the following claims.

We claim:

1. A method for isolating microvesicles from or reducing the microvesicle content of a liquid sample comprising:
   a) obtaining a liquid sample comprising intact microvesicles;
   b) contacting said liquid sample comprising intact microvesicles with porous siliceous beads under conditions suitable to allow for porous siliceous bead-intact microvesicle complex formation, thereby creating a porous siliceous bead-intact microvesicle complex admixture;
   c) incubating said porous siliceous bead-intact microvesicle complex admixture for a period of time sufficient to allow for porous siliceous bead-intact microvesicle complex formation; and
   d) separating said porous siliceous bead-intact microvesicle complex admixture to obtain a porous siliceous bead-intact microvesicle complex fraction and a liquid fraction, wherein said liquid fraction comprises reduced microvesicle content as compared to said liquid sample of step (a), thereby isolating microvesicles from or reducing the microvesicle content of said liquid sample.

2. The method of claim 1, wherein the porous siliceous beads are diatomaceous earth.

3. The method of claim 1, wherein the porous siliceous beads are perlite.

4. The method of claim 1, wherein the pore size of the porous siliceous beads is about 0.1 to 10 microns, optionally about 0.2 to 5 microns, optionally about 0.5 to 2 microns, optionally about 1 micron.

5. The method of claim 1, wherein the microvesicles comprise exosomes, low density lipoprotein (LDL) particles and/or a population of microvesicles possessing an average diameter of between about 40 nm and about 150 nm.

6. The method of claim 1, wherein the microvesicles comprise Aquaporin-2 (AQ-2).

7. The method of claim 1, wherein obtaining step (a) comprises centrifuging a urine sample from the subject to remove cells and/or cell debris, thereby creating (i) a first pellet containing said cells and/or cell debris and (ii) a first supernatant, wherein the first supernatant is provided as the liquid sample to step (b).

8. The method of claim 1, wherein:
   the porous siliceous bead-intact microvesicle complex admixture is present in an array of porous siliceous bead-intact microvesicle complex admixtures, optionally wherein the array is a 96 well array;
   the porous siliceous bead-intact microvesicle complex admixture volume is less than about 1 ml;
   said separating (d) comprises centrifugation, optionally wherein said centrifugation creates a pellet that is resuspended in a solution;
   said separating step (d) comprises an ultracentrifuge spin at speed >75,000×g; and/or
   said centrifuging step (d) comprises a low speed centrifugation spin below 18,000×g, optionally centrifugation at about 2,000×g.

9. A method for isolating microvesicles from or reducing the microvesicle content of a liquid sample from a subject or cell culture comprising:
   a) obtaining a liquid sample comprising intact microvesicles from a subject or cell culture;
   b) centrifuging the liquid sample comprising intact microvesicles from the subject or cell culture to remove cells, cell debris and/or mucus, thereby creating (i) a first pellet containing said cells, cell debris and/or mucus, and (ii) a first supernatant comprising intact microvesicles;
   c) removing said first pellet;
   d) contacting said first supernatant comprising intact microvesicles with porous beads under conditions suitable to allow for porous bead-intact microvesicle complex formation, thereby creating an admixture;
   e) incubating said admixture for a period of time sufficient to allow for porous bead-intact microvesicle complex formation; and
   f) separating said admixture to obtain a porous bead-intact microvesicle complex fraction and a liquid fraction, thereby isolating microvesicles from or reducing the microvesicle content of the liquid sample from the subject or cell culture.

10. The method of claim 9, wherein the porous beads are porous siliceous beads, optionally diatomaceous earth or perlite, optionally wherein the pore size of the porous beads is about 0.1 to 10 microns, optionally about 0.2 to 5 microns, optionally about 0.5 to 2 microns, optionally about 1 micron.

11. The method of claim 9, wherein the liquid sample comprises a biofluid, optionally wherein the liquid sample comprises a fluid selected from the group consisting of whole blood, blood serum, blood plasma, urine, saliva, sputum, breast milk, ascites fluid, synovial fluid, amniotic fluid, semen, cerebrospinal fluid, follicular fluid and tears.

12. The method of claim 9, wherein the liquid sample comprises serum, optionally wherein said serum is selected from the group consisting of a bovine serum, a horse serum, a human serum, a rat serum, a mouse serum, a rabbit serum, a sheep serum, a goat serum, a lamb serum, a chicken serum and a porcine serum, optionally wherein said serum is in vitro cell culture serum, optionally wherein said serum is a fetal bovine serum.

13. The method of claim 9, wherein said separating step comprises centrifugation.

14. The method of claim 9, wherein the admixture is present in an array of admixtures, optionally wherein the array is a 96 well array, optionally wherein the admixture volume is less than about 1 ml.

15. The method of claim 9, wherein the liquid sample comprises urine.

16. The method of claim 7, wherein the urine sample is contacted with tris(2-carboxyethyl)phosphine (TCEP), optionally wherein said TCEP is immobilized on beads.

17. The method of claim 1, wherein the liquid sample comprises a biofluid, optionally wherein the liquid sample comprises a fluid selected from the group consisting of whole blood, blood serum, blood plasma, urine, saliva, sputum, breast milk, ascites fluid, synovial fluid, amniotic fluid, semen, cerebrospinal fluid, follicular fluid and tears.

18. The method of claim 1, wherein the liquid sample comprises serum, optionally wherein said serum is selected from the group consisting of a bovine serum, a horse serum, a human serum, a rat serum, a mouse serum, a rabbit serum, a sheep serum, a goat serum, a lamb serum, a chicken serum and a porcine serum, optionally wherein said serum is in vitro cell culture serum, optionally wherein said serum is a fetal bovine serum.

19. The method of claim 1, wherein separating step (d) further comprises removing said liquid fraction from said porous siliceous bead-intact microvesicle complex fraction, optionally wherein separating step (d) further comprises resuspending said porous siliceous bead-intact microvesicle complex fraction in a solution, thereby producing a microvesicle enriched solution.

20. The method of claim 9, wherein the microvesicles comprise exosomes, low density lipoprotein (LDL) particles and/or population of microvesicles possessing an average diameter of between about 40 nm and about 150 nm, optionally wherein the microvesicles comprise Aquaporin-2 (AQ-2).

21. The method of claim 9, wherein either or both of said centrifuging step (b) and said separating step (f) comprises centrifugation that creates a pellet that is resuspended in a solution, optionally wherein said separating step (0 comprises an ultracentrifuge spin at speed >75,000×g and/or a low-speed centrifugation, optionally centrifugation at about 2,000×g.

22. The method of claim 1, wherein the microvesicles are exosomes.

23. The method of claim 9, wherein the microvesicles are exosomes.

* * * * *